US011913011B2

(12) United States Patent
Davey et al.

(10) Patent No.: US 11,913,011 B2
(45) Date of Patent: Feb. 27, 2024

(54) PLANTS COMPRISING WHEAT G-TYPE CYTOPLASMIC MALE STERILITY RESTORER GENES AND USES THEREOF

(71) Applicants: BASF SE, Ludwigshafen am Rhein (DE); Commonwealth Scientific and Industrial Research Organisation, Acton (AU)

(72) Inventors: Mark Davey, Ghent (BE); Antje Rohde, Ghent (BE); Ruvini Ariyadasa, Ghent (BE); Aswinkumar Singaram Natarajan, Acton (AU); Alexander Whan, Acton (AU); Jonny Jacobs, Ghent (BE); Colin Robert Cavanagh, Bardon (AU); Michel Van Thournout, Ghent (BE); Arne Verstichele, Ghent (BE); Andrew Spriggs, Acton (AU); William Bovill, Acton (AU); Jose Barrero Sanchez, Acton (AU)

(73) Assignees: BASF SE, Ludwigshafen am Rhein (DE); Commonwealth Scientific and Industrial Research Organisation, Acton (AU)

( * ) Notice: Subject to any disclaimer, the term of this patent is extended or adjusted under 35 U.S.C. 154(b) by 89 days.

(21) Appl. No.: 17/058,062

(22) PCT Filed: May 24, 2019

(86) PCT No.: PCT/EP2019/063463
§ 371 (c)(1),
(2) Date: Nov. 23, 2020

(87) PCT Pub. No.: WO2019/224353
PCT Pub. Date: Nov. 28, 2019

(65) Prior Publication Data
US 2021/0155953 A1 May 27, 2021

(30) Foreign Application Priority Data
May 25, 2018 (EP) .................................... 18174269

(51) Int. Cl.
C12N 15/82 (2006.01)
A01H 6/46 (2018.01)
A01H 5/10 (2018.01)
A01H 1/02 (2006.01)

(52) U.S. Cl.
CPC ......... *C12N 15/8289* (2013.01); *A01H 1/023* (2021.01); *A01H 5/10* (2013.01); *A01H 6/4678* (2018.05)

(58) Field of Classification Search
None
See application file for complete search history.

(56) References Cited

U.S. PATENT DOCUMENTS

| 7,094,958 B2 * | 8/2006 | Yu ....................... C12N 15/8216 800/320.2 |
| 2019/0078118 A1 | 3/2019 | Rohde et al. |
| 2019/0082628 A1 | 3/2019 | Rohde et al. |
| 2019/0185879 A1 | 6/2019 | Rohde et al. |
| 2019/0256865 A1 | 8/2019 | Rohde et al. |
| 2020/0347104 A1 * | 11/2020 | Varenne ............. C12N 15/8289 |

FOREIGN PATENT DOCUMENTS

| WO | 2017158126 A1 | 9/2017 |
| WO | 2017158128 A2 | 9/2017 |
| WO | 2018015403 A1 | 1/2018 |
| WO | 2018015404 A1 | 1/2018 |
| WO | 2019086510 A1 | 5/2019 |

OTHER PUBLICATIONS

Shen et al. Structural basis for specific single-stranded RNA recognition by designer pentatricopeptide repeat proteins. Nat. Commun. Apr. 18, 2016; 7:11285. (Year: 2016).*
Ahmed, et al., "QTL analysis of fertility-restoration against cytoplasmic male sterility in wheat", Genes and Genetic Systems, vol. 76, Issue 1, 2001, pp. 33-38.
Bahl, et al., "Chromosomal Location of Male Fertility Restoring Genes in Six Lines of Common Wheat", Crop Science, vol. 13, Issue 3, May 1, 1973, pp. 317-320.
Du, et al., "Genetic Analyses of Male-Fertility Restoration in Wheat: III. Effects of Aneuploidy", Crop Science, vol. 31, Issue 2, Mar. 1, 1991, pp. 319-322.
E. H. Talaat, "Chromosomal location of genes controlling pollen fertility restoration in three restorer lines of wheat", Egyptian Journal of Genetics, vol. 2, 1973, pp. 195-205.
G.C.M. Sage, "Nucleo-Cytoplasmic Relationships in Wheat", Advances in Agronomy, vol. 28, 1976, pp. 267-300.
Hitoshi Kihara, "Substitution of Nucleus and its Effects on Genome Manifestations", Cytologia, vol. 16, Issue 2, 1951, pp. 177-193.
Kojima, et al., "High-resolution RFLP mapping of the fertility restoration (RF3) gene against Triticum timopheevi cytoplasm located on chromosome 1BS of common wheat", Genes & Genetic Systems, vol. 72, Issue 6, 1997, pp. 353-359.
Ma, et al., "Genetic Analysis of Fertility Restoration in Wheat Using Restriction Fragment Length Polymorphisms", Crop Science, vol. 35, Issue 4, Jul. 1, 1995, pp. 1137-1143.
Ma, et al., "Incorporation of restoring gene of Aegilops umbellulata into wheat", Genome, vol. 34, Issue 5, Oct. 1, 1991, pp. 727-732.
Mukai, et al., "Basic studies on hybrid wheat breeding", Theoretical and Applied, vol. 54, Jul. 1979, pp. 153-160.

(Continued)

*Primary Examiner* — Cynthia E Collins
(74) *Attorney, Agent, or Firm* — ArentFox Schiff LLP

(57) ABSTRACT

Methods are described for selecting or producing a cereal plant comprising a functional restorer gene for wheat G-type cytoplasmic male sterility and nucleic acids and/or polypeptides for use therein.

27 Claims, 2 Drawing Sheets

Specification includes a Sequence Listing.

(56) References Cited

OTHER PUBLICATIONS

Robertson, et al., "Monosomic Analysis of Fertility-Restoration in Common Wheat (*Triticum aestivum* L.)", Crop Science, vol. 7, Issue 5, Sep. 1, 1967, pp. 493-495.

Sinha, et al., "Genetic analysis and molecular mapping of a new fertility restorer gene Rf8 for Triticum timopheevi cytoplasm in wheat (*Triticum aestivum* L.) using SSR markers", Genetica, vol. 141, Oct. 16, 2013, pp. 431-441.

Tahir, et al., "Monosomic analysis of *Triticum spelta* var. *Duhamelianum*, a fertility-restorer for T. Timopheevi cytoplasm", Japanese Journal of Genetic, vol. 44, Issue 1, 1969, pp. 1-9.

Yen, et al., "Monosomic Analysis Of Fertility Restoration In Three Restorer Lines Of Wheat", Canadian Journal of Genetics and Cytology, vol. 11, Issue 3, Sep. 1, 1969, pp. 531-546.

Zhang, et al., "Location of the fertility restorer gene for T-Type CMS wheat by microsatellite marker", Acta Genetica Sinica, vol. 30, Issue 5, Jun. 2003, pp. 459-464.

Zhou, et al., "SSR markers associated with fertility restoration genes against Triticum timopheevii cytoplasm in Triticum aestivum", Euphytica, vol. 141, Jan. 2005, pp. 33-40.

Geyer, et al., "Exploring the Genetics of Fertility Restoration Controlled by Rf1 in common wheat (*Triticum aestivum* L.) Using High-density Linkage Maps," Molecular Genetics and Genomics, vol. 293, No. 2, Nov. 2017, pp. 451-462.

Fujii, et al., "Selection Patterns on Restorer-like Genes Reveal a Conflict between Nuclear and Mitochondrial Genomes Throughout Angiosperm Evolution," PNAS, vol. 108, No. 4, Jan. 2011, pp. 1723-1728.

International Search Report issued in PCT/EP2019/063463, dated Jul. 22, 2019, pp. 1-3.

Geyer, et al., "Distribution of the Fertility-Restoring Gene Rf3 in Common and Spelt Wheat Determined by an Informative SNP Marker," Mol. Breeding, vol. 36, No. 167, 2016, pp. 1-11.

Melonek, et al., "The Genetic Basis of Cytoplasmic Male Sterility and Fertility Restoration in Wheat," Nature Communications, vol. 12, No. 1036, 2021, https://doi.org/10.1038/s41467-021-21225-0, pp. 1-14.

\* cited by examiner

SEQUENCE LISTING

```
<160> NUMBER OF SEQ ID NOS: 7

<210> SEQ ID NO 1
<211> LENGTH: 7923
<212> TYPE: DNA
<213> ORGANISM: Triticum aestivum
<220> FEATURE:
<221> NAME/KEY: misc_feature
<222> LOCATION: (1)..(1000)
<223> OTHER INFORMATION: genomic region upstream of the cDNA/mRNA of
      RF1-PPR-09
<220> FEATURE:
<221> NAME/KEY: 5'UTR
<222> LOCATION: (1001)..(1054)
<220> FEATURE:
<221> NAME/KEY: misc_feature
<222> LOCATION: (1055)..(3433)
<223> OTHER INFORMATION: coding region
<220> FEATURE:
<221> NAME/KEY: 3'UTR
<222> LOCATION: (3434)..(3956)
<223> OTHER INFORMATION: 3' UTR part 1
<220> FEATURE:
<221> NAME/KEY: 3'UTR
<222> LOCATION: (4827)..(4919)
<223> OTHER INFORMATION: 3' UTR part 2
<220> FEATURE:
<221> NAME/KEY: 3'UTR
<222> LOCATION: (5398)..(5515)
<223> OTHER INFORMATION: 3' UTR part 3
<220> FEATURE:
<221> NAME/KEY: 3'UTR
<222> LOCATION: (5662)..(5708)
<223> OTHER INFORMATION: 3' UTR part 4
<220> FEATURE:
```

```
<221> NAME/KEY: 3'UTR
<222> LOCATION: (5854)..(6466)
<223> OTHER INFORMATION: 3' UTR part 5
<220> FEATURE:
<221> NAME/KEY: misc_feature
<222> LOCATION: (5854)..(6466)
<223> OTHER INFORMATION: genomic region downstream of cDNA/mRNA
      transcript of RF1-PPR-09

<400> SEQUENCE: 1
cggaggtgat ctggaggcaa tctgagtggg tgcccgtgaa gatgcccctt ctacgacggc      60
cagtgagcga tcctcctcca tgttaccgtg agaaccctaa tcttgtcgat gctcttctcc     120
tgtagctctt ctaatatgcc ataactctgc cataatcaat agttgtagtc cttgatttac     180
tttgatttgc ataacggtgc tacggacacg gcaaaaagga cacaccaccg gcgacaacat     240
acccgccgaa gttggagctt gcttcgccgc gccggtggcg gtgctgacga tgctgccatg     300
ctcctcatct tcagttgttt ccttgccgag gagcttgaag ttccggccat ggataggttt     360
agggcacacg agagagcaga tttggggaag aaataaagtc agggactggg gaatgagaag     420
gtaatgttca taagggggttt tctgtaaaaa gaaagagcaa cctaagcgac cccttttgtcg     480 acttggcgtg ggtcaatgcg ccacacaggc aggtcaatga gcgcttgtga gaaaaaggtc     540
ctcgggtaaa ccacttgctt aaagaattac tccctccgtc ccatattata agaacgtttt     600
tgacactagt gtagtgtcaa aaacgttctt atattatggg acggagggag tagtacctaa     660
aggtgcattt tggactaaat aagactaaag tgacacccag acgaaacttt taggacctcg     720
agtgcatcta actcttaaaa aaacaaagat gctaaaaaac taaatgctta aaaatatatt     780
tttctatggg aatacttaaa aatactatta taattttatg gcttcctagt atatttctag     840
ggcttacaac taaatttata ttcttggtct aaataaaatt ataatctgat aaattatgtg     900
atatgaatat gtcatatagg catatgagac cataatttaa ttttacctgc aaaaaataag     960
taatagtagt agtactacta gataagataa cttggtaaag cactagcccc gtcgtctccc    1020
agttcaggat ctacctacac tgcacaccaa ggccatgcct cgcttctcct ccaccacgcc    1080
aatgtcgcca ccccgcctcc tcctccggct cggcgcccgc cactcctcct ccacctctca    1140
tccctcacgc atctgggatc cccacgccgc cttcgccgct gcgacgcagc gggcgcgctc    1200
tggcacgctc accacggagg acgcacacca cctgtttgat gaattgctgc ggcagggcaa    1260
tcctgtccag gagcgtccct tgactaactt tctggctgcc ctcgcccgcg cgcccgcgtc    1320
cgcattctgc agcgatggcc ctgccctggc cgtcgccctc ttcggccgtt tgtcccgagg    1380
cgccggacga cgggtggcgc agccaaatgt cttcacctat ggcgtcctca tggactgctg    1440
ctgccgtgcg cgccgcctgg atctagcgat cgccttcttc gcccgtctcc tcaagacggg    1500
actggaggca aaccaagtca tcttctgcac cctcctcaag ggactctgcc acgcaaagcg    1560
ctcagatgag gctttggacg tggtgcttca caggatgcct gagctaggct gcaccccaa    1620 cgtggtggcc tataccacgg tcatccacgg cttcttgaag gaaggccaag taggcaaggc    1680
atgcaatcta ttccatggaa tggcgcagca gggcgttgcg cctgatgtgg tgacatataa    1740
ctcggttatc gatgcgttgt gcaaggccag agcaatggac aaggcagagt atttccttcg    1800
tgaaatggtt gataatggtg tcgtacctaa taatgtgaca tataatagcc tcatccatgg    1860
atattcctct ttgggccatc agaaggaggc tgttagggtg ctgaaagaaa tgacaagaca    1920
gggtatcata ccagatgtca ttacctgcac ctcactcatg accttccttt gcaagaatgg    1980
aaaaagcaag gaagctgcag aaattttttga ttcaatggcc acgaagggcc tgaaacatga    2040
```

```
cgccgtttca tatgctattc tccttcatgg gtatgccact gaaggatgct tggttgatat    2100
gattaatctc ttcaattcga tggacagaga ctgtattcta cctaactgtc atatcttcaa    2160
catactgatt tatgcatatg ctaaatctgg gaagcttgat aaggctatgc ttatatttag    2220
agatatgcag aaacaaggag tgagcccaga tgcattcaca tattcaacct aatacatgc     2280 attttgtaaa aagggtcggt tggacgatgc tatgataaag tttaatcaga tggttgatac    2340
aggagtacga cagggcacag ctgtttatgg ttctctaatc cagggttttt gtacacacgg    2400
cgatttggtg aaaggaaagg aattggttac tgaaatgatg aacaaaggta tacctcctcc    2460
tgacattatg ttcttccatt caatcatgca gaacctatgc acagaaggaa gggtagtaga    2520
agcacgggat atccttggct tgatagcaca cataggtatg aggcctaatg tttgcacatt    2580
taatatactg attggtggat actgcctagt ccgcaagatg gaggatgcct caaaaatatt    2640
tcatgatatg atgtcatatg gtttagaacc ttctaatgtt acgtatggta ttcttattaa    2700
tggctattgc aaaaacagaa ggattgatga cgggctgatt ctgttcaaag aaatgttgcg    2760
caagggactt aaacctacaa cttttaatta caacatcata ctggatggat tatttctggc    2820
tggacgaact gttgctgcaa aggaaaagtt tgatgagatg gttgaatctg gagtaagtat    2880
gtgcatcagt acttactcta tagttcttcg tggactttgt agaaataatt gtagcggcga    2940
agccatcacg ctattccaga cattaagcgc aatggatgtg aaattcaata ttagaattgt    3000
caatatcatg attgatgcct tcttcagggt tcagcgaaag caagaagcta aggatttgtt    3060
tgctgcaata acagccaatg ggttggttgc taatgttttt acctacagcc taatgatgac    3120 aaaatcttata aaagaagggt cagtggaaga ggctgacaca ctctttttat cgatggagat    3180
gagcggctgt acttcgaact cgtggatgtt aaatcttatt atcagagggt gctggaaaa     3240 aggagagata gtcaaggctg atgttatat gtctaaagtt gatgcgaaga gctactcact     3300
tgaagctaaa actgtttcgt tgctgatcta tctcttttca gggaaaggga aatacagaga    3360
acacataaga ttgctaccta caaagtatca gtttctcgaa gaagcagcca cagttgaatg    3420
gtttgctata tgatatctgg acgtaactcc tagaagctaa acttgagttg ttacttgcca    3480
taggttctcc tgcttttgca acaaatgcct tcatatgtg taaatagaaa gtcagcttat    3540
aagaagccgt caggatggca gagagagaac aaatcaaacg cactccaaaa caaaagagaa    3600
acctcgccaa actgaatcca aactcaaaca ggtgcatcat caaaagtccg aagctgtact    3660
gtttgctagc caaactccta cgggagattg tcaggcggcc gggcatgaag tggcaggcgt    3720
ctatgcgcct tcgctgctgc cagcatccat ggcttagcat cacacggaat tgagtcaacc    3780
aattcccagc gagtttgggc gcctccattg aagatgcaac cgtttctagc cgccaaatac    3840
gcctaagggt cagagtaatc agcgagcatg ccccttttgt ctggttcgag aagaatttga    3900
agaagctagc agcaacagga gcttgaccgg tttgttctca tcaaagccag tttaaggtta    3960
gttaattata acatggtaat aaagaggtgt tttgttgact gttgaggtgt aatatgttat    4020
atgccaagct cttgatgatt agggtgacct gtgaagcatg caaaagtctg aatcatatgt    4080
gcttgttagt tattttggca acttttagt cttttccca tgtacagatt ttatggatcc       4140
atttgaagta gtatgtacat tctggcatta aatatgaggt gtagaggttt acttaaggac    4200
cggtctgcaa aaaaaatttt gatcgaggca gcaccacgtt gagtttaacc ctgtaacttg    4260
gctcacctcg atcatgctag tgttatcgcc ggaaattgta ttatcactgg gctcagcgtt    4320
tttttacatt gaattaaaca tactctgtgg ttgcagaaac tgactccaaa cagtgttcac    4380
agttaatatg gctctgtcgg taattttcat tgactgtcaa catgttcctt ttttgaaaag    4440
```

```
taggctggcc agttgtcgtt cagtactctg tatataatga tgctaagact gacaaggata    4500
tgacggatgg atttgagctt ctttgccata gttcaaagtg tgcagtctgg gttatgcttt    4560
atattatttt cttttggctt tggtagtatg aacaggaagc aggcaggaac gaactgatat    4620
gtggtactat attttgttat ggaatctagt tgttgttgtt gttatcatta ttattattgt    4680
catcataatc attatccctt ttctccaaga aaagtgtgcc ctaaattata gatcagttca    4740
ttcatctcgc ctctttttt aggggccata gtctgatgga ttttgaagag cttctccatg    4800
gttttctctt ctgttccttg gtgcagggcc tggtggaatt atgctgaact gtaacatttt    4860
ggtactacag aaaagttctt cttaagttgg tcgctttggg ggcacattac atgtttgagg    4920
tactctaatt tttccttggc atgtctagac cttgaatatg gtttgtatta atgcactgtt    4980
attattcaaa ttacagatat ctaattttgt ggaagtttat tttctgactc cctagatatc    5040
ctgttttagt tgtactatta aaggaaaagg actaccttat atttcaccca tgactttctt    5100
tttggaatca gctgtaccat tttataataa attatgtacg atgaaaatgt taacaataaa    5160
ccacaccagc tcaaattgtt tgcgaagctg aatcttaact gatgtgaggt catattgttc    5220
ttgatctttt aaaagtgtac cttgtgaata atttggcatg tctaccacat tacctggtta    5280
atgccctgct gagtttagtt tcataatgca tggactgtgt tttatcatgt taattaaacc    5340
tgtgcatttc ctcaactttt atttggtatc ttcagctaat gccatatgac catccagatg    5400
aacttctctg tggagaaaaa ttgggtggcc tgtccatttg cccctatgtc ttcttatgtc    5460
tgcgattgtt gaactgtagc tttgcgcggg ccactcctcc aacaattacg gccttgtgag    5520
ttctaatgaa tagccccccc ccccccccc ccctacatt tatttgcagt caaattcttg    5580
tagagttgcc ccagaaaatg aagatagaaa agaaacaagt gtacagttga atgtatgacg    5640
attgtttcgt cttccttgca gaaaccactc atccagtgaa ctggctgtta aaatcgatgc    5700
ttcttttggt gagctgatat tagttgatca ctcaatgctc agtccctccc gttaaacttc    5760
agtaacaaat taccccagaa agatcataat actggcctga ctaattcaag taaacatggt    5820
aagtattctg aaatttctgt ttttgagttt cagatcacac cttggacaa gattattccg    5880 gagccgttgg tgctgatgca gcaagaaaga taggggttct gaagtgcaat aagacaaggt    5940
atccagaaga tctaataatt gatatgaccg atggatattc aggggctttc ttttatgtaa    6000
agggcaggtg tactaccaat tcattctagt ggagaaaaca ttggtactag cattatttgc    6060
acgctcaaag gttgacagac gaaaccagtt aaaataatac tcctacctcc attccaaaat    6120
ataagtagcc taccaaaacg tcttgaattt tggaatgggg gtaatatatc aaaggatcat    6180
cactcctaat ggttggcagc tgatcactga ttagggtgga gtcgtcgatt gataaactgg    6240
cgcatgcttt actgtattgc agtgatgtca aatgccacag ttctctgtaa tacaacttaa    6300
actgaacact cacctgttcc ttcttaactc tgtcatgtac tgtagaagag tagctgtgtg    6360
atatcatggc ccttgatttt attttggatt gccagatgca gactgcttaa gttgcagtag    6420
cagtcataac tgcaccagat atgtgtccta tttttataga agtgatgtgg gtcagtcgac    6480
ttgtgagtgc aaacttactc ttgtgtgacc tgttggatct ttatcgcata gctaagaaca    6540
tatactccct ctgttccaaa ataaaggtg catttgtttt ttccaatttt tttgcaaatt    6600
tgaccaagtt tttagaaaaa aatatagcaa tatctgcagt agtaaatttg tatcattaga    6660
tccatcacga aaagtatttt catatttttat atttgtacta gcccaaatac ccgtgcatcg    6720
caatgggaca aaatttttaag gtgtatttcg atttttaagca acacgcattc caaaatccac    6780
```

```
tcaattgcac cgttcaaata atagtataaa tttggattcc aaatgctgta gttgactaat    6840
tattttagca gtgttgcctt attttcgtga tagttgggcc ggctaagttg gagcacgggt    6900
tgtgaaaggc ctaggtcgag ctacgtgcac cacgcgagga tctcttcgtt ggcacaaacc    6960
tccctacaaa acactcttat ggtctgcggg tttatcctct caaaaatatg cttttatggt    7020
ctacagattt aatttgccaa ataaaaggat tttttgacgg agcggacatt ttttgaatgg    7080
atgaatgttt tttgattttt gtgaacgttt tctcaaattc attttcaaat tcaagaatat    7140
tatttgaata catgatcatt ttaaaaaaat catcactttt ttatttcccg aacatagttt    7200
tcgaaattgt gatttttca  taatatgcaa acaacttttg aaaatcacca gcatttttt     7260 aatttgcaaa cattttatga tttcccgaac atatcttcaa ttcttaaaat tttatgattt    7320
ctcaaacttt tattttcaaa ttttcaactt aaaaattaga ttttttggaa atactaaatt    7380
aatattaaaa acaaaaacaa aaattagaaa tagaaaagaa aaagcaagaa aatggaatga    7440
aaatggaatg aaaaagggga cggggacgtc acccccgca  catgggccgc cccatgaacg    7500
cgtgggagga ggaggtacat gcttggtttt agagagaaaa aagggagata aataggctta    7560
atacagagct ggagacaaca agtatgaggc acgctctaaa aaaaccttc  cgatatgagt    7620 gtatgtggga aacaaaggaa gattttcatc aagtagtgga ggaagcctgg aaccgtaatc    7680
aaccttctct ttcagtttcg gacctagctg ccaagctcag ttcagtttct gtagcgctag    7740
ctcagtgggg acgcaggtct tttggatcag tccggcagga gctgcgtctg ttgcgacatc    7800
agctagctac cctacgggca gtaccgggtc gggtgggccc aagtgagaag gagaagcgag    7860
tccaagatcg catgatcgaa gtttctctgg cggaggagat catgatgagg cagagatcac    7920
gaa                                                                 7923
```

<210> SEQ ID NO 2
<211> LENGTH: 895
<212> TYPE: DNA
<213> ORGANISM: Triticum aestivum x Triticum timopheevi

<400> SEQUENCE: 2

```
tcttccagcg tttagtattc aagttcttct cttccagccc cccggcccct ctttgataag      60
gaaagtttgc atttctcaaa taaaaaatga caaatatggt tcgatggctc ttctccacta     120
gcaggtttac tgcttttctat ttgcactttt gtattaagtt tccttatata tacgattttt    180
tattattttc tatttgtcta ttttttcttt tagtgcgttt tatttcgatt attcttctcc     240
caatttgcaa tcttttcgga gcctccttca ttattactct tcctcagag  attcaggatc     300 cccaagctct agctcattta gcagggctaa acttctatct gagcctttac gagcaggatc     360
ctggatgggt tacgttcatt cagaacgagc ttaatcacaa tacccctctg gaggacatac     420
ctggacggct taagctcttc ctaatggaag aaaagctgtc tagtatgcga caagatgtca     480
ttcaggaatt tgtggcgctt tatcaaagaa tagggcctta tctaccgatc gagcccctact   540 tggtcgatga agcgcttcgt tcctatctgg accatattca cgcaactgat tctttcactg    600
ttctccaagc gtcttatcaa gatctgcggg agaatgaggg aggatctgtt tctttagag    660 atgctgtttc ccacaaccgg gatctccttg aggcggaaag ctccgcaagg aggtgcctgg    720
aagtggaaca gaggatccga tgggaagaaa tccccaagag caaggcaagt ctcgaaagag    780
ctgagcacga gcatgctctc gacttgttta agtcggagga tcttagaagg gaattagaaa    840 aaaaagagc ggggtagctc agtaattctg attcttttct cttccagccc ccggg           895
```

<210> SEQ ID NO 3
<211> LENGTH: 16
<212> TYPE: DNA
<213> ORGANISM: Artificial Sequence
<220> FEATURE:
<223> OTHER INFORMATION: predicted target sequence within ORF256

<400> SEQUENCE: 3
atttgtctat ttttct                                                      16

<210> SEQ ID NO 4
<211> LENGTH: 3827
<212> TYPE: DNA
<213> ORGANISM: Triticum aestivum
<220> FEATURE:
<221> NAME/KEY: 5'UTR
<222> LOCATION: (1)..(54)
<220> FEATURE:
<221> NAME/KEY: CDS
<222> LOCATION: (55)..(2433)
<220> FEATURE:
<221> NAME/KEY: 3'UTR
<222> LOCATION: (2434)..(3827)

<400> SEQUENCE: 4

```
cactagcccc gtcgtctccc agttcaggat ctacctacac tgcaccaa ggcc atg          57
                                                         Met
                                                         1 cct cgc ttc tcc tcc acc acg cca atg tcg cca ccc cgc ctc ctc ctc       105
Pro Arg Phe Ser Ser Thr Thr Pro Met Ser Pro Pro Arg Leu Leu Leu
        5                  10                  15 cgg ctc ggc gcc cgc cac tcc tcc tcc acc tct cat ccc tca cgc atc       153
Arg Leu Gly Ala Arg His Ser Ser Ser Thr Ser His Pro Ser Arg Ile
         20                  25                  30 tgg gat ccc cac gcc gcc ttc gcc gct gcg acg cag cgg gcg cgc tct       201
Trp Asp Pro His Ala Ala Phe Ala Ala Ala Thr Gln Arg Ala Arg Ser
     35                  40                  45 ggc acg ctc acc acg gag gac gca cac cac ctg ttt gat gaa ttg ctg       249
Gly Thr Leu Thr Thr Glu Asp Ala His His Leu Phe Asp Glu Leu Leu
50                  55                  60                  65 cgg cag ggc aat cct gtc cag gag cgt ccc ttg act aac ttt ctg gct       297
Arg Gln Gly Asn Pro Val Gln Glu Arg Pro Leu Thr Asn Phe Leu Ala
                 70                  75                  80 gcc ctc gcc cgc gcg ccc gcg tcc gca ttc tgc agc gat ggc cct gcc       345
Ala Leu Ala Arg Ala Pro Ala Ser Ala Phe Cys Ser Asp Gly Pro Ala
             85                  90                  95 ctg gcc gtc gcc ctc ttc ggc cgt ttg tcc cga ggc gcc gga cga cgg       393
Leu Ala Val Ala Leu Phe Gly Arg Leu Ser Arg Gly Ala Gly Arg Arg
        100                 105                 110 gtg gcg cag cca aat gtc ttc acc tat ggc gtc ctc atg gac tgc tgc       441
Val Ala Gln Pro Asn Val Phe Thr Tyr Gly Val Leu Met Asp Cys Cys
    115                 120                 125 tgc cgt gcg cgc cgc ctg gat cta gcg atc gcc ttc ttc gcc cgt ctc       489
Cys Arg Ala Arg Arg Leu Asp Leu Ala Ile Ala Phe Phe Ala Arg Leu
130                 135                 140                 145 ctc aag acg gga ctg gag gca aac caa gtc atc ttc tgc acc ctc ctc       537
Leu Lys Thr Gly Leu Glu Ala Asn Gln Val Ile Phe Cys Thr Leu Leu
                150                 155                 160 aag gga ctc tgc cac gca aag cgc tca gat gag gct ttg gac gtg gtg       585
Lys Gly Leu Cys His Ala Lys Arg Ser Asp Glu Ala Leu Asp Val Val
            165                 170                 175 ctt cac agg atg cct gag cta ggc tgc acc ccc aac gtg gtg gcc tat       633
Leu His Arg Met Pro Glu Leu Gly Cys Thr Pro Asn Val Val Ala Tyr
        180                 185                 190
```

-continued

```
acc acg gtc atc cac ggc ttc ttg aag gaa ggc caa gta ggc aag gca      681
Thr Thr Val Ile His Gly Phe Leu Lys Glu Gly Gln Val Gly Lys Ala
    195                 200                 205 tgc aat cta ttc cat gga atg gcg cag cag ggc gtt gcg cct gat gtg      729
Cys Asn Leu Phe His Gly Met Ala Gln Gln Gly Val Ala Pro Asp Val
210                 215                 220                 225 gtg aca tat aac tcg gtt atc gat gcg ttg tgc aag gcc aga gca atg      777
Val Thr Tyr Asn Ser Val Ile Asp Ala Leu Cys Lys Ala Arg Ala Met
                230                 235                 240 gac aag gca gag tat ttc ctt cgt gaa atg gtt gat aat ggt gtc gta      825
Asp Lys Ala Glu Tyr Phe Leu Arg Glu Met Val Asp Asn Gly Val Val
            245                 250                 255 cct aat aat gtg aca tat aat agc ctc atc cat gga tat tcc tct ttg      873
Pro Asn Asn Val Thr Tyr Asn Ser Leu Ile His Gly Tyr Ser Ser Leu
        260                 265                 270 ggc cat cag aag gag gct gtt agg gtg ctg aaa gaa atg aca aga cag      921
Gly His Gln Lys Glu Ala Val Arg Val Leu Lys Glu Met Thr Arg Gln
    275                 280                 285 ggt atc ata cca gat gtc att acc tgc acc tca ctc atg acc ttc ctt      969
Gly Ile Ile Pro Asp Val Ile Thr Cys Thr Ser Leu Met Thr Phe Leu
290                 295                 300                 305 tgc aag aat gga aaa agc aag gaa gct gca gaa att ttt gat tca atg     1017
Cys Lys Asn Gly Lys Ser Lys Glu Ala Ala Glu Ile Phe Asp Ser Met
                310                 315                 320 gcc acg aag ggc ctg aaa cat gac gcc gtt tca tat gct att ctc ctt     1065
Ala Thr Lys Gly Leu Lys His Asp Ala Val Ser Tyr Ala Ile Leu Leu
            325                 330                 335 cat ggg tat gcc act gaa gga tgc ttg gtt gat atg att aat ctc ttc     1113
His Gly Tyr Ala Thr Glu Gly Cys Leu Val Asp Met Ile Asn Leu Phe
        340                 345                 350 aat tcg atg gac aga gac tgt att cta cct aac tgt cat atc ttc aac     1161
Asn Ser Met Asp Arg Asp Cys Ile Leu Pro Asn Cys His Ile Phe Asn
    355                 360                 365 ata ctg att tat gca tat gct aaa tct ggg aag ctt gat aag gct atg     1209
Ile Leu Ile Tyr Ala Tyr Ala Lys Ser Gly Lys Leu Asp Lys Ala Met
370                 375                 380                 385 ctt ata ttt aga gat atg cag aaa caa gga gtg agc cca gat gca ttc     1257
Leu Ile Phe Arg Asp Met Gln Lys Gln Gly Val Ser Pro Asp Ala Phe
                390                 395                 400 aca tat tca acc tta ata cat gca ttt tgt aaa aag ggt cgg ttg gac     1305
Thr Tyr Ser Thr Leu Ile His Ala Phe Cys Lys Lys Gly Arg Leu Asp
            405                 410                 415 gat gct atg ata aag ttt aat cag atg gtt gat aca gga gta cga cag     1353
Asp Ala Met Ile Lys Phe Asn Gln Met Val Asp Thr Gly Val Arg Gln
        420                 425                 430 ggc aca gct gtt tat ggt tct cta atc cag ggt ttt tgt aca cac ggc     1401
Gly Thr Ala Val Tyr Gly Ser Leu Ile Gln Gly Phe Cys Thr His Gly
    435                 440                 445 gat ttg gtg aaa gga aag gaa ttg gtt act gaa atg atg aac aaa ggt     1449
Asp Leu Val Lys Gly Lys Glu Leu Val Thr Glu Met Met Asn Lys Gly
450                 455                 460                 465 ata cct cct cct gac att atg ttc ttc cat tca atc atg cag aac cta     1497
Ile Pro Pro Pro Asp Ile Met Phe Phe His Ser Ile Met Gln Asn Leu
                470                 475                 480 tgc aca gaa gga agg gta gta gaa gca cgg gat atc ctt ggc ttg ata     1545
Cys Thr Glu Gly Arg Val Val Glu Ala Arg Asp Ile Leu Gly Leu Ile
            485                 490                 495 gca cac ata ggt atg agg cct aat gtt tgc aca ttt aat ata ctg att     1593
Ala His Ile Gly Met Arg Pro Asn Val Cys Thr Phe Asn Ile Leu Ile
```

```
                500               505               510
ggt gga tac tgc cta gtc cgc aag atg gag gat gcc tca aaa ata ttt    1641
Gly Gly Tyr Cys Leu Val Arg Lys Met Glu Asp Ala Ser Lys Ile Phe
    515                 520                 525 cat gat atg atg tca tat ggt tta gaa cct tct aat gtt acg tat ggt    1689
His Asp Met Met Ser Tyr Gly Leu Glu Pro Ser Asn Val Thr Tyr Gly
530                 535                 540                 545 att ctt att aat ggc tat tgc aaa aac aga agg att gat gac ggg ctg    1737
Ile Leu Ile Asn Gly Tyr Cys Lys Asn Arg Arg Ile Asp Asp Gly Leu
        550                 555                 560 att ctg ttc aaa gaa atg ttg cgc aag gga ctt aaa cct aca act ttt    1785
Ile Leu Phe Lys Glu Met Leu Arg Lys Gly Leu Lys Pro Thr Thr Phe
            565                 570                 575 aat tac aac atc ata ctg gat gga tta ttt ctg gct gga cga act gtt    1833
Asn Tyr Asn Ile Ile Leu Asp Gly Leu Phe Leu Ala Gly Arg Thr Val
                580                 585                 590 gct gca aag gaa aag ttt gat gag atg gtt gaa tct gga gta agt atg    1881
Ala Ala Lys Glu Lys Phe Asp Glu Met Val Glu Ser Gly Val Ser Met
                    595                 600                 605 tgc atc agt act tac tct ata gtt ctt cgt gga ctt tgt aga aat aat    1929
Cys Ile Ser Thr Tyr Ser Ile Val Leu Arg Gly Leu Cys Arg Asn Asn
610                 615                 620                 625 tgt agc ggc gaa gcc atc acg cta ttc cag aca tta agc gca atg gat    1977
Cys Ser Gly Glu Ala Ile Thr Leu Phe Gln Thr Leu Ser Ala Met Asp
        630                 635                 640 gtg aaa ttc aat att aga att gtc aat atc atg att gat gcc ttc ttc    2025
Val Lys Phe Asn Ile Arg Ile Val Asn Ile Met Ile Asp Ala Phe Phe
            645                 650                 655 agg gtt cag cga aag caa gaa gct aag gat ttg ttt gct gca ata aca    2073
Arg Val Gln Arg Lys Gln Glu Ala Lys Asp Leu Phe Ala Ala Ile Thr
                660                 665                 670 gcc aat ggg ttg gtt gct aat gtt ttt acc tac agc cta atg atg aca    2121
Ala Asn Gly Leu Val Ala Asn Val Phe Thr Tyr Ser Leu Met Met Thr
                    675                 680                 685 aat ctt ata aaa gaa ggg tca gtg gaa gag gct gac aca ctc ttt tta    2169
Asn Leu Ile Lys Glu Gly Ser Val Glu Glu Ala Asp Thr Leu Phe Leu
690                 695                 700                 705 tcg atg gag atg agc ggc tgt act tcg aac tcg tgg atg tta aat ctt    2217
Ser Met Glu Met Ser Gly Cys Thr Ser Asn Ser Trp Met Leu Asn Leu
        710                 715                 720 att atc aga ggg ttg ctg gaa aaa gga gag ata gtc aag gct gga tgt    2265
Ile Ile Arg Gly Leu Leu Glu Lys Gly Glu Ile Val Lys Ala Gly Cys
            725                 730                 735 tat atg tct aaa gtt gat gcg aag agc tac tca ctt gaa gct aaa act    2313
Tyr Met Ser Lys Val Asp Ala Lys Ser Tyr Ser Leu Glu Ala Lys Thr
                740                 745                 750 gtt tcg ttg ctg atc tat ctc ttt tca ggg aaa ggg aaa tac aga gaa    2361
Val Ser Leu Leu Ile Tyr Leu Phe Ser Gly Lys Gly Lys Tyr Arg Glu
                    755                 760                 765 cac ata aga ttg cta cct aca aag tat cag ttt ctc gaa gaa gca gcc    2409
His Ile Arg Leu Leu Pro Thr Lys Tyr Gln Phe Leu Glu Glu Ala Ala
770                 775                 780                 785 aca gtt gaa tgg ttt gct ata tga tatctggacg taactcctag aagctaaact   2463
Thr Val Glu Trp Phe Ala Ile
                    790 tgagttgtta cttgccatag gttctcctgc ttttgcaaca aatgccttc atatgtgtaa   2523 atagaaagtc agcttataag aagccgtcag gatggcagag agagaacaaa tcaaacgcac   2583 tccaaaacaa aagagaaacc tcgccaaact gaatccaaac tcaaacaggt gcatcatcaa   2643
```

```
aagtccgaag ctgtactgtt tgctagccaa actcctacgg gagattgtca ggcggccggg    2703
catgaagtgg caggcgtcta tgcgccttcg ctgctgccag catccatggc ttagcatcac    2763
acggaattga gtcaaccaat tcccagcgag tttgggcgcc tccattgaag atgcaaccgt    2823
ttctagccgc caaatacgcc taagggtcag agtaatcagc gagcatgccc cttttgtctg    2883
gttcgagaag aatttgaaga agctagcagc aacaggagct tgaccggttt gttctcatca    2943
aagccagttt aagggcctgg tggaattatg ctgaactgta acattttggt actacagaaa    3003
agttcttctt aagttggtcg ctttgggggc acattacatg tttgagatga acttctctgt    3063
ggagaaaaat tgggtggcct gtccatttgc ccctatgtct tcttatgtct gcgattgttg    3123
aactgtagct ttgcgcgggc cactcctcca acaattacgg ccttaaacca ctcatccagt    3183
gaactggctg ttaaaatcga tgcttctttt gatcacacct ttggacaaga ttattccgga    3243
gccgttggtg ctgatgcagc aagaaagata ggggttctga agtgcaataa gacaaggtat    3303
ccagaagatc taataattga tatgaccgat ggatattcag gggctttctt ttatgtaaag    3363
ggcaggtgta ctaccaattc attctagtgg agaaacactt ggtactagca ttatttgcac    3423
gctcaaaggt tgacagacga aaccagttaa aataatactc ctacctccat tccaaaatat    3483
aagtagccta ccaaaacgtc ttgaattttg gaatgggggt aatatatcaa aggatcatca    3543
ctcctaatgg ttggcagctg atcactgatt agggtggagt cgtcgattga taaactggcg    3603
catgctttac tgtattgcag tgatgtcaaa tgccacagtt ctctgtaata caacttaaac    3663
tgaacactca cctgttcctt cttaactctg tcatgtactg tagaagagta gctgtgtgat    3723
atcatggccc ttgattttat tttggattgc cagatgcaga ctgcttaagt tgcagtagca    3783
gtcataactg caccagatat gtgtcctatt tttatagaag tgat               3827
```

<210> SEQ ID NO 5
<211> LENGTH: 792
<212> TYPE: PRT
<213> ORGANISM: Triticum aestivum

<400> SEQUENCE: 5

```
Met Pro Arg Phe Ser Ser Thr Thr Pro Met Ser Pro Pro Arg Leu Leu
1               5                   10                  15

Leu Arg Leu Gly Ala Arg His Ser Ser Ser Thr Ser His Pro Ser Arg
            20                  25                  30

Ile Trp Asp Pro His Ala Ala Phe Ala Ala Thr Gln Arg Ala Arg
        35                  40                  45

Ser Gly Thr Leu Thr Thr Glu Asp Ala His His Leu Phe Asp Glu Leu
    50                  55                  60

Leu Arg Gln Gly Asn Pro Val Gln Glu Arg Pro Leu Thr Asn Phe Leu
65                  70                  75                  80

Ala Ala Leu Ala Arg Ala Pro Ala Ser Ala Phe Cys Ser Asp Gly Pro
                85                  90                  95

Ala Leu Ala Val Ala Leu Phe Gly Arg Leu Ser Arg Gly Ala Gly Arg
            100                 105                 110

Arg Val Ala Gln Pro Asn Val Phe Thr Tyr Gly Val Leu Met Asp Cys
        115                 120                 125

Cys Cys Arg Ala Arg Arg Leu Asp Leu Ala Ile Ala Phe Phe Ala Arg
    130                 135                 140

Leu Leu Lys Thr Gly Leu Glu Ala Asn Gln Val Ile Phe Cys Thr Leu
145                 150                 155                 160
```

```
Leu Lys Gly Leu Cys His Ala Lys Arg Ser Asp Glu Ala Leu Asp Val
            165                 170                 175

Val Leu His Arg Met Pro Glu Leu Gly Cys Thr Pro Asn Val Val Ala
        180                 185                 190

Tyr Thr Thr Val Ile His Gly Phe Leu Lys Glu Gly Gln Val Gly Lys
            195                 200                 205

Ala Cys Asn Leu Phe His Gly Met Ala Gln Gln Gly Val Ala Pro Asp
210                 215                 220

Val Val Thr Tyr Asn Ser Val Ile Asp Ala Leu Cys Lys Ala Arg Ala
225                 230                 235                 240

Met Asp Lys Ala Glu Tyr Phe Leu Arg Glu Met Val Asp Asn Gly Val
            245                 250                 255

Val Pro Asn Asn Val Thr Tyr Asn Ser Leu Ile His Gly Tyr Ser Ser
            260                 265                 270

Leu Gly His Gln Lys Glu Ala Val Arg Val Leu Lys Glu Met Thr Arg
        275                 280                 285

Gln Gly Ile Ile Pro Asp Val Ile Thr Cys Thr Ser Leu Met Thr Phe
        290                 295                 300

Leu Cys Lys Asn Gly Lys Ser Lys Glu Ala Ala Glu Ile Phe Asp Ser
305                 310                 315                 320

Met Ala Thr Lys Gly Leu Lys His Asp Ala Val Ser Tyr Ala Ile Leu
            325                 330                 335

Leu His Gly Tyr Ala Thr Glu Gly Cys Leu Val Asp Met Ile Asn Leu
            340                 345                 350

Phe Asn Ser Met Asp Arg Asp Cys Ile Leu Pro Asn Cys His Ile Phe
        355                 360                 365

Asn Ile Leu Ile Tyr Ala Tyr Ala Lys Ser Gly Lys Leu Asp Lys Ala
        370                 375                 380

Met Leu Ile Phe Arg Asp Met Gln Lys Gln Gly Val Ser Pro Asp Ala
385                 390                 395                 400

Phe Thr Tyr Ser Thr Leu Ile His Ala Phe Cys Lys Lys Gly Arg Leu
            405                 410                 415

Asp Asp Ala Met Ile Lys Phe Asn Gln Met Val Asp Thr Gly Val Arg
            420                 425                 430

Gln Gly Thr Ala Val Tyr Gly Ser Leu Ile Gln Gly Phe Cys Thr His
        435                 440                 445

Gly Asp Leu Val Lys Gly Lys Glu Leu Val Thr Glu Met Met Asn Lys
        450                 455                 460

Gly Ile Pro Pro Asp Ile Met Phe Phe His Ser Ile Met Gln Asn
465                 470                 475                 480

Leu Cys Thr Glu Gly Arg Val Val Glu Ala Arg Asp Ile Leu Gly Leu
            485                 490                 495

Ile Ala His Ile Gly Met Arg Pro Asn Val Cys Thr Phe Asn Ile Leu
            500                 505                 510

Ile Gly Gly Tyr Cys Leu Val Arg Lys Met Glu Asp Ala Ser Lys Ile
        515                 520                 525

Phe His Asp Met Met Ser Tyr Gly Leu Glu Pro Ser Asn Val Thr Tyr
        530                 535                 540

Gly Ile Leu Ile Asn Gly Tyr Cys Lys Asn Arg Arg Ile Asp Asp Gly
545                 550                 555                 560

Leu Ile Leu Phe Lys Glu Met Leu Arg Lys Gly Leu Lys Pro Thr Thr
            565                 570                 575

Phe Asn Tyr Asn Ile Ile Leu Asp Gly Leu Phe Leu Ala Gly Arg Thr
```

```
                    580                 585                 590
Val Ala Ala Lys Glu Lys Phe Asp Glu Met Val Glu Ser Gly Val Ser
                595                 600                 605

Met Cys Ile Ser Thr Tyr Ser Ile Val Leu Arg Gly Leu Cys Arg Asn
            610                 615                 620

Asn Cys Ser Gly Glu Ala Ile Thr Leu Phe Gln Thr Leu Ser Ala Met
625                 630                 635                 640

Asp Val Lys Phe Asn Ile Arg Ile Val Asn Ile Met Ile Asp Ala Phe
                645                 650                 655

Phe Arg Val Gln Arg Lys Gln Glu Ala Lys Asp Leu Phe Ala Ala Ile
                660                 665                 670

Thr Ala Asn Gly Leu Val Ala Asn Val Phe Thr Tyr Ser Leu Met Met
            675                 680                 685

Thr Asn Leu Ile Lys Glu Gly Ser Val Glu Ala Asp Thr Leu Phe
            690                 695                 700

Leu Ser Met Glu Met Ser Gly Cys Thr Ser Asn Ser Trp Met Leu Asn
705                 710                 715                 720

Leu Ile Ile Arg Gly Leu Leu Glu Lys Gly Glu Ile Val Lys Ala Gly
                725                 730                 735

Cys Tyr Met Ser Lys Val Asp Ala Lys Ser Tyr Ser Leu Glu Ala Lys
                740                 745                 750

Thr Val Ser Leu Leu Ile Tyr Leu Phe Ser Gly Lys Gly Lys Tyr Arg
            755                 760                 765

Glu His Ile Arg Leu Leu Pro Thr Lys Tyr Gln Phe Leu Glu Glu Ala
            770                 775                 780

Ala Thr Val Glu Trp Phe Ala Ile
785                 790

<210> SEQ ID NO 6
<211> LENGTH: 20
<212> TYPE: DNA
<213> ORGANISM: Artificial Sequence
<220> FEATURE:
<223> OTHER INFORMATION: Forward primer qPCR

<400> SEQUENCE: 6
ctaagggtca gagtaatcag                                             20

<210> SEQ ID NO 7
<211> LENGTH: 20
<212> TYPE: DNA
<213> ORGANISM: Artificial Sequence
<220> FEATURE:
<223> OTHER INFORMATION: reverse primer qPCR

<400> SEQUENCE: 7
tgatgagaac aaaccggtca                                             20
```

PLANTS COMPRISING WHEAT G-TYPE CYTOPLASMIC MALE STERILITY RESTORER GENES AND USES THEREOF

CROSS-REFERENCE TO RELATED APPLICATIONS

This application is a National Stage Entry of PCT/EP2019/063463, filed May 24, 2019, which claims foreign priority to EP Patent Application No. 18174269.3, filed on May 25, 2018, the disclosures of which are hereby incorporated by reference in their entireties.

FIELD OF THE INVENTION

The present invention relates generally to the field of plant breeding and molecular biology and concerns a method for selecting or producing a cereal plant comprising a restorer gene for wheat G-type cytoplasmic male sterility, and nucleic acids for use therein.

BACKGROUND

Cytoplasmic male sterility ("CMS") is a major trait of interest in cereals such as wheat in the context of commercial hybrid seed production (Kihara, 1951, Cytologia 16, 177-193); Wilson and Ross, Wheat Inf Serv. (Kyoto) 14:29-30, 1962; Lucken, 1987 (Hybrid wheat. In Wheat and wheat improvement. Edited by E. G. Heyne. American Society of Agronomy, Madison, Wis.); Sage, 1976, Adv. Agron. 28, 265-298). The cytoplasms of *Triticum timopheevii* (G-type) and *Aegilops kotschyi* (K-type) are widely studied as inducers of male sterility in common wheat (*Triticum aestivum*), due to few deleterious effects (Kaul, Male sterility in higher plants. Springer Verlag, Berlin 1988; Lucken, 1987, supra; Mukai and Tsunewaki, Theor. Appl. Genet. 54, 1979).

In hybrid seed production systems using G-type cytoplasm, restoration of cytoplasmic male sterility is a critical problem. Most hexaploid wheat varieties do not naturally contain fertility restoration ("Rf") genes (Ahmed et al. 2001, Genes and Genetic Systems 76, 33-38). In the complicated restoration system of *T. timopheevii*, eight Rf loci have been reported to restore the fertility of cytoplasmic male sterile *T. timopheevii* cytoplasm, and the chromosome locations of these loci have been determined as: Rf1 (Chr 1A), Rf2 (Chr 7D), Rf3 (Chr 1B), Rf4 (Chr 6B), Rf5 (Chr 6D), Rf6 (Chr 5D), Rf7 (Chr 7B) and Rf8 (Tahir & Tsunewaki, 1969, Jpn J Genet 44: 1-9; Yen et al., Can. J. Genet. Cytol. 11, 531-546, 1969; Bahl & Maan, Crop Sci. 13, 317-320, 1973; Du et al. Crop Sci, 31: 319-22, Crop 1991; Sinha et al., Genetica 2013, http://dx.doi.org/10.1007/s10709-013-9742-5). Ma et al. (Genome 34:727-732, 1991) transferred an Rf gene locus from *Aegilops umbellulata* to wheat; two independent translocation lines with the Rf locus being located on either chromosome 6AS or 6BS were created (from Zhou et al., 2005, Euphytica 141(1-2):33-40, doi: 10.1007/s10681-005-5067-5).

Zhang et al., (Acta Genetica Sinica 06/2003; 30(5):459-64.) describe an Rf locus located on 1AS in restorer line 7269-10, with the genetic distance between the SSR marker Xgwm136 and this Rf gene being 6.7 cM.

WO2017158126A1 and WO2017158128A1 have provided more accurate markers to identify and track the Rf1 locus on chromosome 1AS, as present for example in wheat line PI 583676 (USDA National Small Grains Collection).

Geyer et al., (2017, Molecular Genetics and Genomics, https://doi.org/10.1007/s00438-017-1396-z, online November 2017) map the same Rf locus as Rf1 in restorer lines R3, R113, and L19 and estimated its effect in populations.

There nevertheless remains a need to identify additional and/or alternative Rf genes which can be used to develop improved methods for fertility restoration in wheat containing *T. timopheevii* cytoplasm, including by combination with other identified Rf genes. The present invention provides a contribution by disclosing an Rf gene from the Rf1 locus on chromosome 1A.

SUMMARY OF THE INVENTION

In one embodiment, the invention provides a(n) (isolated or modified) nucleic acid molecule(s) encoding a functional restorer of fertility gene (Rf) allele for wheat G-type cytoplasmic male sterility, wherein the functional restorer gene allele is a functional allele of a pentatricopeptide repeat protein (PPR) gene comprised within the nucleotide sequence of SEQ ID NO: 1. The functional restorer gene may comprise a nucleotide sequence selected from a nucleotide sequence having at least 85% sequence identity to SEQ ID NO: 4 from the nucleotide at position 55 to the nucleotide at position 2433; a nucleotide sequence having at least 85% sequence identity to SEQ ID NO: 4; or a nucleotide sequence encoding a polypeptide comprising an amino acid sequence having at least 85% sequence identity to SEQ ID NO: 5. The functional restorer gene allele may encode a PPR protein capable of binding to the mRNA of ORF256, preferably to a nucleotide sequence comprising nt 105-121 of SEQ ID NO: 2, although the PPR protein may also be capable of interacting with other sites on orf256, or with other mitochondrial and/or organellar transcripts or peptides, and may be obtainable from USDA accession number PI 583676. The nucleotide sequence of SEQ ID NO. 4 may also be transcribed at least 2-fold higher, or at least 5-fold higher or at least 10-fold higher in wheat lines with a functional Rf1 restorer, than in non-Rf1 lines, although in most instances the difference observed consists of significant detection of transcription in wheat lines with a functional Rf1 restorer and no detectable transcription in non-Rf1 lines.

In another embodiment of the invention, a(n) (isolated or modified) polypeptide is provided encoded by the nucleic acid molecules described herein, or comprising an amino acid sequence having at least 85% sequence identity to the amino acid sequence of SEQ ID NO: 5, preferably over the entire length of the polypeptide.

In yet another embodiment of the invention, a chimeric gene is provided comprising the following operably linked elements (a) a plant-expressible promoter; (b) a nucleic acid comprising the nucleic acid molecule herein described or encoding the polypeptide herein described; and optionally (c) a transcription termination and polyadenylation region functional in plant cells, wherein at least one of the operably linked elements is heterologous with respect to at least one other element, or contains a modified sequence. Thus, the plant-expressible promoter (a) may be heterologous with respect to the nucleic acid encoding the polypeptide herein described (b) or may be heterologous with respect to the transcription termination and polyadenylation region (c), when the latter is present, or the nucleic acid encoding the polypeptide herein described (b) may be heterologous with respect to the transcription termination and polyadenylation region (c), when the latter is present. The plant expressible promoter may be capable of directing expression of the operably linked nucleic acid at least during (early) pollen development and meiosis, such as in anther or, more specifically, tapetum, or developing microspores.

The invention further provides cereal plant cells or cereal plants or seeds thereof, such as wheat plant cells or plant or seed thereof, comprising the nucleic acid molecules or the polypeptides or the chimeric genes herein described, preferably wherein the polypeptide, the nucleic acid, or the chimeric gene in each case is heterologous with respect to the plant cell or plant or seed.

It is yet another embodiment of the invention to provide a method for producing a cereal plant cell or plant or seed thereof, such as a wheat plant cell or plant or seed thereof, comprising a functional restorer gene for wheat G-type cytoplasmic male sterility, or for increasing restoration capacity for wheat G-type cytoplasmic male sterility ("CMS") in a cereal plant or cell, such as a wheat plant, comprising the step of providing the plant cell or plant with the nucleic acid molecules or the chimeric genes herein described, it being understood that the step of providing comprises providing by transformation, crossing, backcrossing, genome editing or mutagenesis. The nucleic acid molecules or the chimeric genes may be transcribed at least 2-fold higher.

The invention further provides a method for producing a cereal plant cell or plant or seed thereof, such as a wheat plant cell or plant or seed thereof, with restoration capacity for wheat G-type cytoplasmic male sterility, or a method for increasing restoration capacity for wheat G-type cytoplasmic male sterility ("CMS") in a cereal plant, such as a wheat plant, comprising the steps of providing or expressing or increasing the expression of one or more polypeptides as herein described in the plant cell or plant or seed. The Rf-PPR polypeptide may be provided by modifying the genome of the plant to comprise the nucleic acid molecule or the chimeric gene herein described wherein the step of modifying includes by transformation, crossing, backcrossing, genome editing or mutagenesis. Further provided herein is a modified nucleic acid encoding a Rf-PPR protein, such as a (modified or isolated) Rf1-PPR-09 protein, wherein said nucleic acid is modified by genome editing or mutagenesis (e.g., EMS mutagenesis).

Also provided is a method for converting a non-restoring cereal plant, such as a wheat plant, into a restoring plant for wheat G-type cytoplasmic male sterility ("CMS"), or for increasing restoration capacity for wheat G-type cytoplasmic male sterility ("CMS") in a cereal plant, such as a wheat plant, comprising the step of modifying the genome of the plant to comprise the nucleic acid molecule or the chimeric gene herein described wherein the step of modifying comprises modifying by transformation, crossing, backcrossing, genome editing or mutagenesis.

In another embodiment, a method is provided for converting a non-restoring cereal plant, such as a wheat plant, into a restoring plant for wheat G-type cytoplasmic male sterility ("CMS"), or for increasing restoration capacity for wheat G-type cytoplasmic male sterility ("CMS") in a cereal plant, such as a wheat plant, comprising the steps of modifying the genome of the plant to increase the expression of a polypeptides as herein described in the plant.

The invention further provides cereal plant cells or cereal plants or seeds thereof, such as a wheat plant cells or plants or seeds thereof, obtained according to the methods herein described, preferably wherein the plant has an increased restoration capacity for wheat G-type cytoplasmic male sterility ("CMS"), preferably wherein Rf-PPR polypeptide described is expressed at least during (early) pollen development and meiosis, such as in anther or, more specifically, tapetum, or developing microspores. The plant cell, plant or seed may be a hybrid plant cell, plant or seed. In one embodiment, such plant has a modified Rf1_PPR_09 nucleic acid and/or protein that results in improved restoration of G-type CMS in a cereal, such as a wheat, plant compared to the restoration obtained with the nucleic acid sequence of SEQ ID NO: 1 or 4 or the protein sequence of SEQ ID NO: 5 in said plant.

In yet another embodiment of the invention, a method for selecting a cereal plant comprising a functional restorer gene allele for wheat G-type cytoplasmic male sterility or for producing a cereal plant comprising a functional restorer gene allele for wheat G-type cytoplasmic male sterility, is provided, comprising the steps of (a) identifying the presence, expression or transcription, such as by transcription analysis, of a nucleotide sequence comprising the nucleotide sequence of SEQ ID NO: 4 from nucleotide position 55 to nucleotide position 2433; and optionally selecting the plant comprising, expressing, or transcribing the nucleotide sequence.

The invention also provides a method for restoring fertility in a progeny of a G-type cytoplasmic male sterile cereal plant or for producing a fertile progeny plant from a G-type cytoplasmic male sterile cereal parent plant, comprising the steps of (a) providing a population of progeny plants obtained from crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility comprising or transcribing the nucleotide sequence of SEQ ID NO: 1 (partially) or SEQ ID NO: 4; (b) identifying in the population a fertile progeny plant comprising or expressing or transcribing the nucleotide sequence of SEQ ID NO: 1 (partially) or SEQ ID NO: 4; and optionally (c) selecting the fertile progeny plant; and optionally (d) propagating the fertile progeny plant.

As another embodiment of the invention, a method is provided for identifying and/or selecting a cereal (e.g. wheat) plant comprising a functional restorer gene allele for wheat G-type cytoplasmic male sterility comprising the steps of (a) identifying or detecting in the plant the presence, expression or transcription of a nucleic acid or of the PPR polypeptide or of chimeric genes as herein provided and optionally selecting the plant comprising, expressing or transcribing the nucleic acid or polypeptide or chimeric gene.

It is also an objective of the invention to provide a method for producing a cereal plant, such as a wheat plant, comprising a functional restorer gene allele for wheat G-type cytoplasmic male sterility, comprising the steps of (a) crossing a first cereal plant as herein described or provided with a second cereal plant; and (b1) identifying a progeny plant comprising, expressing or transcribing a functional restorer gene allele for wheat G-type cytoplasmic male sterility comprising the nucleotide sequence of SEQ ID NO: 4; or (b2) identifying and selecting a progeny plant comprising, expressing or transcribing a functional restorer gene allele for wheat G-type cytoplasmic male sterility comprising the nucleotide sequence of SEQ ID NO: 4.

It is a further objective of the invention to provide a method for producing hybrid seed, comprising the steps of: (a) providing a male cereal parent plant, such as a wheat plant as herein provided, the plant comprising or expressing the functional restorer gene allele for wheat G-type cytoplasmic male sterility, wherein the functional restorer gene allele is preferably present in homozygous form; (b) providing a female cereal parent plant that is a G-type cytoplasmic male sterile cereal plant, and (c) crossing the female cereal parent plant with a the male cereal parent plant; or (a) providing a male cereal parent plant, such as a wheat plant as herein provided, the plant comprising or expressing the functional restorer gene allele for wheat G-type cytoplasmic male sterility, wherein the functional restorer gene allele is preferably present in homozygous form; (b) providing a female cereal parent plant that is a G-type cytoplasmic male sterile cereal plant, (c) crossing the female cereal parent plant with a the male cereal parent plant; and (d) harvesting seeds.

The invention also provides use of the nucleic acid as herein described to identify one or more further functional restorer gene alleles for wheat G-type cytoplasmic male sterility.

Further provided are uses of nucleic acids, polypeptides or chimeric genes as herein described for the identification of a plant comprising and/or expressing a functional restorer gene allele for wheat G-type cytoplasmic male sterility.

The plants comprising and/or expressing the functional restorer gene for wheat G-type cytoplasmic male sterility as herein described may be used for restoring fertility in a progeny of a G-type cytoplasmic male sterile cereal plant, such as a wheat plant and/or for producing hybrid seed or a population of hybrid cereal plants, such as wheat seed or plants.

DETAILED DESCRIPTION

Figure 1:
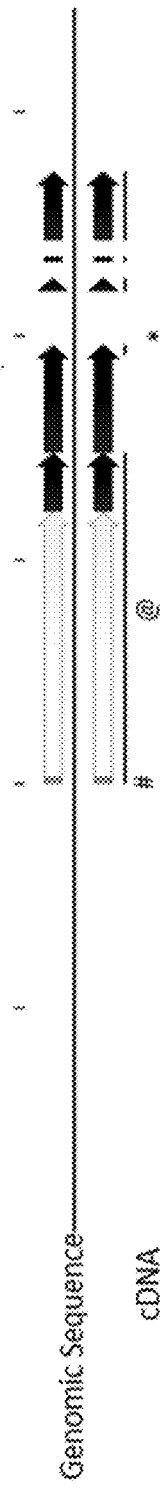
FIG. 1: (A)—Predicted gene structure for the identified Rf1-PPR-09 gene. @ indicates CDS, # indicates 5' UTR, and * indicates 3' UTR (B) amino acid sequence of identified Rf1-PPR-09 gene indicating the transit peptide (italic) and the PPR motifs (alternatingly underlined and not underlined) including the 5th and 35th amino acid implied in RNA recognition (bold). (C) Graphical representation of the structure of the Rf1-PPR-09 polypeptide with PPR motifs.
Figure 1:
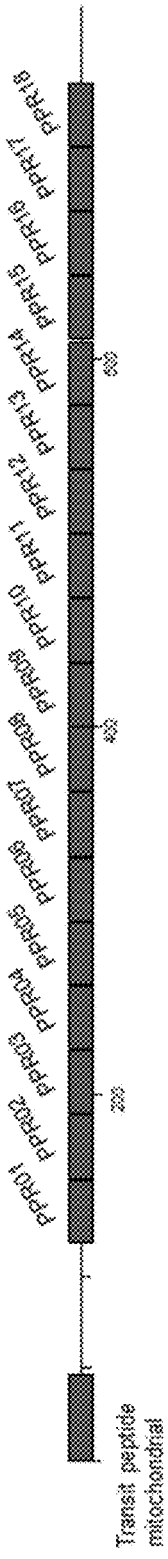

The present invention describes the identification of a functional restorer (R$^f$) gene for wheat G-type cytoplasmic male sterility (i.e., lines containing *T. timopheevii* cytoplasm) located on chromosome 1A (short arm 1AS), as well as methods to detect the Rf gene. These methods can be used in marker-assisted selection (MAS) of cereal plants, such as wheat, comprising said functional restorer genes located on chromosomes 1A. The identification of the gene is therefore extremely useful in methods for hybrid seed production, as it can be used e.g. in a method for restoring fertility in progeny of a plant possessing G-type cytoplasmic male sterility, thereby producing fertile progeny plants from a G-type cytoplasmic male sterile parent plant. Likewise, the present disclosure also allows the identification of plants lacking the desired gene, so that non-restorer plants can be identified and, e.g., eliminated from subsequent crosses. The identification of a restorer gene underlying the Rf1 locus on chromosome 1AS further allows targeted engineering to e.g. increase expression thereof, or increased activity, or targeted combination of the gene underlying the Rf1 locus with other restorer loci or genes.

Another use of knowledge of the gene underlying the Rf1 locus in plant breeding is to assist the recovery of the recurrent parent genotype by backcross breeding. Backcross breeding is the process of crossing a progeny back to one of its parents. Backcrossing is usually done for the purpose of introgressing one or several loci from a donor parent into an otherwise desirable genetic background from the recurrent parent. The more cycles of backcrossing that are performed, the greater the genetic contribution of the recurrent parent to the resulting variety. This is often necessary, because donor parent plants may be otherwise undesirable, e.g., due to low yield, low fecundity or the like. In contrast, varieties which are the result of intensive breeding programs may have excellent yield, fecundity or the like, merely being deficient in one desired trait such as fertility restoration. As a skilled worker understands, backcrossing can be done to select for or against a trait. For example, in the present invention, one can select a restorer gene for breeding a restorer line or one can select against a restorer gene for breeding a maintainer (female pool) line.

The Rf1 locus on chromosome 1A was mapped to a segment along the chromosome 1A, in an interval of about 15.6 cM. Further fine-mapping narrowed the 1A-region to an interval of about 1.9 cM (from 30.9 to 32.8 cM along chromosome 1A) (see published PCT application WO2017/158126—incorporated herein by reference in its entirety).

Male sterility in connection with the present invention refers to the failure or partial failure of plants to produce functional pollen or male gametes. This can be due to natural or artificially introduced genetic predispositions or to human intervention on the plant in the field. Male fertile on the other hand relates to plants capable of producing sufficient levels of functional pollen and male gametes, preferably normal levels. Male sterility/fertility can be reflected in fertile/viable seed set upon selfing, e.g. by bagging heads to induce self-fertilization. Likewise, fertility restoration can also be described in terms of seed set upon crossing a male sterile plant with a plant carrying a functional restorer gene, when compared to seed set resulting from crossing (or selfing) fully fertile plants. Partial failure to produce pollen or male gametes preferably refers to plants which produce less than 20%, less than 15% or less than 10% fertile seed upon selfing, or even less than 5%.

A male parent or pollen parent, is a parent plant that provides the male gametes (pollen) for fertilization, while a female parent or seed parent is the plant that provides the female gametes for fertilization, said female plant being the one bearing the seeds.

Cytoplasmic male sterility or "CMS" as used herein refers to cytoplasmic-based and maternally-inherited male sterility. CMS is total or partial male sterility in plants as the result of specific nuclear and mitochondrial interactions and is maternally inherited via the cytoplasm. Male sterility is the failure or partial failure of plants to produce functional anthers, pollen, or male gametes although CMS plants still produce viable female gametes. Partial failure to produce pollen or male gametes preferably refers to plants which produce less than 20%, less than 15% or less than 10% fertile seed upon selfing, or even less than 5%. Cytoplasmic male sterility is used in agriculture to facilitate the production of hybrid seed. Cytoplasmic male-sterility ("CMS") is caused by one or more mutations in the mitochondrial genome (termed "sterile cytoplasm") and is inherited as a dominant, maternally-transmitted trait. For cytoplasmic male sterility to be used in hybrid seed production, the seed parent must contain a sterile cytoplasm and the pollen parent must contain (nuclear) restorer genes (Rf genes) to restore the fertility of the hybrid plants grown from the hybrid seed. Accordingly, such Rf genes are preferably at least partially dominant, most preferably dominant, in order to have sufficient restoring ability in the offspring.

"Wheat G-type cytoplasmic male sterility", as used herein refers to the cytoplasm of *Triticum timopheevii* that can confer male sterility when introduced into common wheat (i.e. *Triticum aestivum*), thereby resulting in a plant carrying common wheat nuclear genes but cytoplasm from *T. timopheevii* that is male sterile. The cytoplasm of *T. timopheevii* (G-type) as inducers of male sterility in common wheat have been extensively studied (Wilson and Ross, 1962, supra; Kaul, Male sterility in higher plants. Springer Verlag, Berlin. 1988; Lucken, Hybrid wheat. In Wheat and wheat improvement. Edited by E. G. Heyne. American Society of Agronomy, Madison, Wis., 1987; Mukai and Tsunewaki, Theor. Appl. Genet. 54, 153-60, 1979; Tsunewaki, Jpn. Soc. Prom. Sci. (Tokyo), 49-101, 1980 (In: Tsunewaki K. (ed.) Genetic diversity of the cytoplasm in *Triticum* and *Aegilops*; Tsunewaki et al., Genes Genet. Syst. 71, 293-311, 1996). The origin of the CMS phenotype conferred by *T. timopheevii* cytoplasm is the expression of a novel chimeric gene/transcript termed orf256, which is located upstream of cox1 sequences and is cotranscribed with an apparently normal cox1 gene. Antisera prepared against polypeptide sequences predicted from the orf256 nucleotide sequence recognized a 7-kDa protein present in the CMS line but not in the parental or restored lines (Song and Hedgcoth, Genome 37(2), 203-209, 1994; Hedgcoth et al., Curr. Genet. 41, 357-365, 2002).

As used herein "a functional restorer gene allele for wheat G-type cytoplasmic male sterility" or "a functional restorer locus for wheat G-type cytoplasmic male sterility" or a "restorer QTL for wheat G-type cytoplasmic male sterility" indicates an allele that has the capacity to restore fertility in the progeny of a cross with a G-type cytoplasmic male sterility ("CMS") line, i.e., a line carrying common wheat nuclear genes but cytoplasm from *T. timopheevii*. Restoration against G-type cytoplasm has e.g. been described by Robertson and Curtis (Crop Sci. 7, 493-495, 1967), Yen et al. (Can. J. Genet. Cytol. 11, 531-546, 1969), Bahl and Maan (Crop Sci. 13, 317-320, 1973), Talaat et al. (Egypt. J. Genet. 2, 195-205, 1973) Zhang et al., (2003, supra) Ma and Sorrels (1995, supra), Kojima (1997, supra), Ahmed et al (2001, supra), Zhou et al (2005, supra). Such restorer genes or alleles are also referred to as Rf genes and Rf alleles. As described at least in the examples, the restorer gene herein described is also more highly expressed, particularly in developing spikes, in wheat lines identified to comprise the Rf1 locus when compared to wheat lines which were identified as not comprising the Rf1 locus or compared to non-restoring wheat lines. The mean relative expression level of the restorer gene in wheat lines identified to comprise the restoring Rf1 locus compared to the mean relative expression level of the restorer gene in wheat lines identified as not comprising the restoring Rf1 locus (particularly mean relative expression level in developing spikes) ranges from about 2 fold to at least about 25 fold higher, such as between 7-fold and 12-fold higher. Usually the ratio is about 10-fold higher. It is expected that protein levels encoded by the Rf1 gene are also increased in wheat lines identified to comprising the restoring Rf1 locus when compared to wheat lines identified as not comprising the restoring Rf1 locus and may equally be at least 2-fold higher, or ranging between about 2-fold to at least about 25-fold higher, such as between 7-fold and 12-fold higher.

The term "maintainer" refers to a plant that when crossed with the CMS plant does not restore fertility, and maintains sterility in the progeny. The maintainer is used to propagate the CMS line, and may also be referred to as a non-restorer line. Maintainer lines have the same nuclear genes as the CMS line (i.e. do not contain functional Rf genes), but differ in the composition of cytoplasmic factors that cause male sterility in plants i.e. maintainers have "fertile" cytoplasm. Therefore when a male sterile line is crossed with its maintainer progeny with the same male sterile genotype will be obtained.

The term "cereal" and "cereal plant" refers to members of the monocotyledonous family Poaceae which are cultivated for the edible components of their grain. These grains are composed of endosperm, germ and bran. Maize, wheat and rice together account for more than 80% of the worldwide grain production. Other members of the cereal plant family comprise rye, oats, barley, triticale, sorghum, wild rice, spelt, einkorn, emmer, durum wheat and kamut. A "female cereal plant" or "cytoplasmic male sterile cereal plant" is a cereal plant comprising cytoplasm causing male sterility, as herein described.

In one embodiment, a cereal plant according to the invention is a cereal plant that comprises at least an A genome or related genome, such as hexaploid wheat (*T. aestivum*; ABD), spelt (*T. spelta*; ABD) durum (*T. turgidum*; AB), barley (*Hordeum vulgare*; H) and rye (*Secale cereale*; R). In a specific embodiment, the cereal plant according to the invention is wheat (*T. aestivum*; ABD).

A particularly useful assay for detection of SNP markers is for example KBioscience Competitive Allele-Specific PCR (KASP, see www.kpbioscience.co.uk), For developing the KASP-assay 70 base pairs upstream and 70 base pairs downstream of the SNP are selected and two allele-specific forward primers and one allele specific reverse primer is designed. See e.g. Allen et al. 2011, Plant Biotechnology J. 9, 1086-1099, especially p 1097-1098 for KASP assay method.

The position of the chromosomal segments identified, and the markers thereof, when expressed as recombination frequencies or map units, are provided herein as a matter of general information. The embodiments described herein were obtained using particular wheat populations. Accordingly, the positions of particular segments and markers as map units are expressed with reference to the used populations. It is expected that numbers given for particular segments and markers as map units may vary from cultivar to cultivar and are not part of the essential definition of the DNA segments and markers, which DNA segments and markers are otherwise described, for example, by nucleotide sequence.

A locus (plural loci), as used herein refers to a certain place or position on the genome, e.g. on a chromosome or chromosome arm, where for example a gene or genetic marker is found. A QTL (quantitative trait locus), as used herein, refers to a position on the genome that corresponds to a measurable characteristic, i.e. a trait, such as the Rf loci.

As used herein, the term "allele(s)", such as in allele of a gene, means any of one or more alternative forms of a gene at a particular locus. In a diploid cell of an organism, alleles of a given gene are located at a specific location or locus (loci plural) on a chromosome. One allele is present on each chromosome of the pair of homologous chromosomes or possibly on homeologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In tetraploid species, two sets of diploid genomes exist, whereby the chromosomes of the two genomes are referred to as "homeologous chromosomes" (and similarly, the loci or genes of the two genomes are referred to as homeologous loci or genes). Likewise, hexaploid species have three sets of diploid genomes, etc. A diploid, tetraploid or hexaploid plant species may comprise a large number of different alleles at a particular locus. The ploidy levels of domesticated wheat species range from diploid (*T. monococcum*, 2n=14, AA), tetraploid (*T. turgidum*, 2n=28, AABB) to hexaploid (*T. aestivum*, 2n=42, AABBDD).

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

An allele of a particular gene or locus can have a particular penetrance, i.e. it can be dominant, partially dominant, co-dominant, partially recessive or recessive. A dominant allele is a variant of a particular locus or gene that when present in heterozygous form in an organism results in the same phenotype as when present in homozygous form. A recessive allele on the other hand is a variant of an allele that in heterozygous form is overruled by the dominant allele thus resulting in the phenotype conferred by the dominant allele, while only in homozygous form leads to the recessive phenotype. Partially dominant, co-dominant or partially recessive refers to the situation where the heterozygote displays a phenotype that is an intermediate between the phenotype of an organism homozygous for the one allele and an organism homozygous for the other allele of a particular locus or gene. This intermediate phenotype is a demonstration of partial or incomplete dominance or penetrance. When partial dominance occurs, a range of phenotypes is usually observed among the offspring. The same applies to partially recessive alleles.

A "contig", as used herein refers to set of overlapping DNA segments that together represent a consensus region of DNA. In bottom-up sequencing projects, a contig refers to overlapping sequence data (reads); in top-down sequencing projects, contig refers to the overlapping clones that form a physical map of the genome that is used to guide sequencing and assembly. Contigs can thus refer both to overlapping DNA sequence and to overlapping physical segments (fragments) contained in clones depending on the context.

In a further embodiment, said functional restorer gene allele is a functional allele of a gene encoding a pentatricopeptide repeat (PPR) protein (i.e. a PPR gene) localising within the genomic region described in WO2017/158126.

PPR proteins are classified based on their domain architecture. P-class PPR proteins possess multiple canonical amino acid motifs, typically consisting of 35 amino acid residues, although the motifs can range between 34 and 36 or even 38 amino acids. PPR proteins may contain a mitochondrial targeting peptide, but normally lack additional domains. Members of this class have functions in most aspects of organelle gene expression. PLS-class PPR proteins have three different types of PPR motifs, which vary in length; P (35 amino acids), L (long, 35-36 amino acids) and S (short, ~31 amino acids), and members of this class are thought to mainly function in RNA editing. Subtypes of the PLS class are categorized based on the additional C-terminal domains they possess (reviewed by Manna et al., 2015, Biochimie 113, p 93-99, incorporated herein by reference).

Most fertility restoration (Rf) genes identified to date, come from a small clade of genes encoding PPR proteins (Fuji et al., 2011, PNAS 108(4), 1723-1728—herein incorporated by reference). PPR genes functioning as fertility restoration (Rf) genes are referred to in Fuji (supra) as Rf-PPR genes. They are comprised primarily of tandem arrays of 15-20 PPR motifs, each composed of about 35 amino acids.

Most Rf-PPR genes belong to the P-class Rf-PPR subfamily, although PLS-class Rf-PPR genes have also been identified. High substitution rates observed for particular amino acids within otherwise very conserved PPR motifs, indicating diversifying selection, prompted the conclusion that these residues might be directly involved in binding to RNA targets. This has led to the proposal of a "PPR code" which allows the prediction of RNA target sequences of naturally occurring PPR proteins as well as the design of synthetic PPR proteins that can bind RNA molecules of interest, whereby sequence specificity is ensured by distinct patterns of hydrogen bonding between each RNA base and the amino acid side chains present at positions 2, and/or 5 and/or 35 in the aligned PPR motif (motif (see Melonek et al., 2016, Nat Sci Report 6:35152, Barkan et al., 2012, PLoS Genet 8(8): e1002910; Barkan and Small 2014, Annu. Rev. Plant Biol. 65:415-442 (https://doi.org/10.1146/annurev-arplant-050213-040159); Miranda, McDermott, and Barkan 2017, Nucleic Acids Res. 46, 2613-2623 (https://doi.org/10.1093/nar/gkx1288); Shen et al. 2016, Nat. Commun. 7, 11285 (https://doi.org/10.1038/ncomms11285); and particularly, Yagi Y, Hayashi S, Kobayashi K, Hirayama T, Nakamura T (2013) Elucidation of the RNA Recognition Code for Pentatricopeptide Repeat Proteins Involved in Organelle RNA Editing in Plants. PLoS ONE 8(3): e57286. doi: 10.1371/journal.pone.0057286, all herein incorporated by reference).

Accordingly, a functional allele of a Rf-PPR gene, as used herein, refers to an allele of a Rf-PPR gene that is a functional restorer gene allele for wheat G-type cytoplasmic male sterility as described herein, i.e. that when expressed in a (sexually compatible) cereal plant has the capacity to restore fertility in the progeny of a cross with a G-type cytoplasmic male sterile cereal plant. Such a functional allele of a Rf-PPR gene is also referred to as a PPR-Rf gene (or Rf-PPR gene), which in turn encodes a PPR-Rf (or Rf-PPR) protein.

Although not intending to limit the invention to a specific mode of action, it is thought that a functional restorer gene allele encodes a polypeptide, such as a PPR protein that has the capacity to (specifically) bind to the mitochondrial orf256 (SEQ ID NO: 2) transcript responsible for the CMS phenotype. By scavenging or otherwise interfering with the orf256 mRNA, the CMS phenotype can be reversed. As used herein, "bind to" or "specifically bind to" or "(specifically) recognize" means that according to the above described PPR code, the PPR protein contains a number of PPR motifs with specific residues at positions 5 and 35 and which are ordered in such a way so as to be able to bind to a target mRNA, such as the orf256 mRNA, in a sequence-specific or sequence-preferential manner.

Alternatively, the functional restorer gene allele may encode a polypeptide, such as a PPR protein that has the capacity to (specifically) bind to other mitochondrial mRNAs or chimeric mRNAs responsible for the pollen lethality and the CMS phenotype. The functional restorer gene allele may also encode a polypeptide, such as a PPR protein that has the capacity to (specifically) bind to multiple mitochondrial mRNAs, influencing transcription etc. Via an another alternative mode of action, the functional restorer gene allele may encode a polypeptide, such as a PPR protein that is able to form a complex with additional interacting proteins such as a glycine rich protein (GRP), a hexokinase, or a DUF-WD40, to direct breakdown or cleavage of orf256 and/or other cytotoxic mitochondrial or plastidic mRNAs, or to inhibit transcription thereof, or to inhibit translation of the cytotoxic, chimeric peptides responsible for the CMS phenotype.

For example, the functional restorer gene allele can encode a PPR protein containing PPR motifs with specific residues at the positions 5 and 35 so as to recognize a target sequence within orf256 mRNA. In one example, the predicted recognition sequence of Rf1-PPR-09 herein described can be defined by a probability matrix (as described in Yagi et al., 2013, supra) and was found to be 5'-ATTTGTCTAT-TTTTCT-3' (SEQ ID NO: 3). Such a sequence is located at a nucleotides 105-121 downstream of the ATG start codon of SEQ ID NO: 2 (orf256 position 192-207). Without intending to limit the invention to a specific mode of action, a possible mechanism for the mode of action of Rf1-PPR-09 protein may be the blocking of the translation of the cytotoxic orf256 transcript, and directing transcription towards cox1 transcription. It is known that in *T. aestivum* lines containing G-type CMS, there is production of long chimeric mRNA transcripts encompassing the orf256 and cox1 gene sequences in a single chimeric mRNA, leading to translation of orf256 and thus production of the cytotoxic ORF256 protein. In restored *T. aestivum* lines containing G-type CMS, then there is still transcription of the long orf256-cox1 RNA, but no longer translation of the ORF256 protein. It is presumed that the binding of Rf1-PPR-09 to its target site prevents translation of the ORF256 in the long chimeric mRNA. (Rathburn H B, & Hedgcoth C, A chimeric open reading frame in the 5' flanking region of cox/mitochondrial DNA from cytoplasmic male-sterile wheat, Plant Mol Biol. 1991 May; 16(5):909-12.; Song J, & Hedgcoth C., Influence of nuclear background on transcription of a chimeric gene (orf256) and Cox1 in fertile and cytoplasmic male sterile wheats. Genome. 1994 April; 37(2):203-9.; Song J & Hedgcoth C., A chimeric gene (orf256) is expressed as protein only in cytoplasmic male-sterile lines of wheat., Plant Mol Biol. 1994 October; 26(1):535-9.; Hedgcoth C, el-Shehawi A M, Wei P, Clarkson M, Tamalis D., A chimeric open reading frame associated with cytoplasmic male sterility in alloplasmic wheat with *Triticum timopheevi* mitochondria is present in several *Triticum* and *Aegilops* species, barley, and rye. Curr Genet. 2002 August; 41(5):357-65)).

Furthermore, PPR proteins may work in conjunction with other PPR proteins, which may be encoded by a gene in the same Rf locus, and/or by a gene located in any of the other Rf loci, including the Rf3 locus identified on chromosome 1B (described in WO2017/158127). In one embodiment, the Rf1_PPR_09 gene is used in cereal plants such as wheat plants in combination with one or more of the Rf loci or Rf genes selected from the group of Rf2, Rf3, Rf4, Rf5, Rf6, Rf7, and Rf8; such as in combination with Rf3 and Rf6, in combination with Rf3 and Rf7, in combination with Rf4 and Rf6, in combination with Rf4 and Rf7, or in combination with Rf3 and Rf4. In one embodiment, such a combination of Rf loci or Rf genes with the Rf1_PPR-09 gene of the invention occurs at the same locus in the wheat genome (e.g., by translocation, transformation or genome engineering into one locus).

A functional restorer gene or allele can for example comprise the nucleotide sequence of SEQ ID NO: 4 or encode a polypeptide having the amino acid sequence of SEQ ID NO: 5.

A functional restorer gene allele can for example also encode a PPR protein, having one or more mutations (insertion, deletion, substitution) that may affect mRNA or protein stability, for example, a mutation that increases mRNA or protein stability, thereby resulting in an increased expression of the PPR protein, especially during early pollen development and meiosis, such as in anther or, more specifically, tapetum, or developing microspore.

In one embodiment, the functional restorer gene allele is a functional allele of the Rf-PPR gene comprising the nucleotide sequence of SEQ ID NO: 4 from nucleotide position 55 to nucleotide position 2433, or SEQ ID NO: 4, or a nucleotide sequence encoding the polypeptide sequence of SEQ ID NO: 5. The functional restorer gene allele can comprise a nucleotide sequence that is substantially identical (as defined herein) to SEQ ID NO: 4, such as having at least 85%, 85.5%, 86%, 87%, 88%, 89%, 90%, 91%, 92%, 93%, 94%, 95%, 96%, 97%, 98%, or 99% sequence identity to SEQ ID NO: 4 from nucleotide position 55 to nucleotide position 2433. The percent sequence identity is preferably calculated over the entire length of the nucleotide sequence of SEQ ID NO: 4 from nucleotide position 55 to nucleotide position 2433 The functional restorer gene allele can also comprise a nucleotide sequence that encodes an amino acid sequence having at least 85%, 86%, 87%, 88%, 89%, 90%, 91%, 92%, 93%, 94%, 95%, 96%, 97%, 98% or 99% sequence identity to SEQ ID NO: 5. The percent sequence identity is preferably calculated over the entire length of the polypeptide of SEQ ID NO: 5.

In a further embodiment, the functional restorer gene allele is a functional restorer gene allele as present in (and as derivable from) at least Accession number PI 583676 (USDA National Small Grains Collection, also known as Dekalb 582M and registered as US PVP 7400045).

The invention further describes a method for producing a cereal (e.g. wheat) plant comprising a functional restorer gene allele for wheat G-type cytoplasmic male sterility, comprising the steps of a. crossing a first cereal plant comprising a functional restorer gene for wheat G-type cytoplasmic male sterility located on chromosome 1A and having a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5, with a second plant;

b. identifying (and optionally selecting) a progeny plant comprising, or comprising and transcribing, the functional restorer gene allele for wheat G-type cytoplasmic male sterility located on chromosome 1A, by identifying a progeny plant comprising at least a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5.

Also provided is a method for producing a cereal plant comprising a functional restorer gene allele for wheat G-type cytoplasmic male sterility located on chromosome 1A, comprising the steps of
   a. crossing a first cereal plant homozygous for a functional restorer gene for wheat G-type cytoplasmic male sterility located on chromosome 1A and having a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5 with a second cereal plant;
   b. obtaining a progeny plant, wherein said progeny plant comprises the functional restorer gene allele for wheat G-type cytoplasmic male sterility located on chromosome 1A defined in step (a).

The second cereal plant may be a plant devoid of a functional restorer gene for wheat G-type cytoplasmic male sterility located on chromosome 1A, including a cereal plant not transcribing or expressing the identified restorer gene.

In an even further embodiment, the invention provides a method for producing F1 hybrid cereal seeds or F1 cereal hybrid plants, comprising the steps of:
   a. providing a male cereal (e.g. wheat) parent plant comprising, or comprising and expressing, a functional restorer gene allele for wheat G-type cytoplasmic male sterility located on chromosome 1A and having a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5;
   b. crossing said male parent plant with a female cereal (e.g. wheat) parent plant, wherein the female parent plant is a G-type cytoplasmic male sterile cereal plant; and
   c. optionally collecting hybrid seeds from said cross.

The F1 hybrid seeds and plants preferably comprise at least one marker allele linked to a functional restorer gene allele for wheat G-type cytoplasmic male sterility located on chromosome 1A as described herein, and the F1 plants grown from the seeds are therefore fertile. Preferably, the male parent plant is homozygous for said functional restorer gene allele for wheat G-type cytoplasmic male sterility located on chromosome 1A.

In the above method, the male parent plant used for crossing can be selected or identified by analyzing the presence, or transcription, or expression, of a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5.

The invention also provides cereal plants, such as wheat plants, obtained by any of the above methods, said cereal plant comprising, expressing or transcribing a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5.

Such plants may contain the functional restorer gene allele for wheat G-type cytoplasmic male sterility in a different genomic context, and may e.g. be devoid of the nucleotide sequence of SEQ ID NO: 1 from position 1 to position 1000 and/or of the nucleotide sequence of SEQ ID NO: 1 from position 6467 to position 7923, or being devoid of any of the following nucleotide sequences, or combinations thereof: the nucleotide sequence of SEQ ID NO: 1 from position 1 to position 500, the nucleotide sequence of SEQ ID NO: 1 from position 1 to position 1000, the nucleotide sequence of SEQ ID NO: 1 from position 6467 to position 7000, the nucleotide sequence of SEQ ID NO: 1 from position 7000 to position 7500 or the nucleotide sequence of SEQ ID NO: 1 from position 7500 to position 7923.

Also provided are plant parts, plant cells and seed from the cereal plants according to the invention comprising or comprising and expressing the functional restorer gene allele. The plants, plant parts, plant cells and seeds of the invention may also be hybrid plants, plant parts, plant cells or seeds.

Also provided is a method to determine the presence or absence of a functional restorer gene allele for wheat G-type cytoplasmic male sterility located on chromosome 1A, or the zygosity status thereof, in a biological sample of a cereal plant, comprising providing genomic DNA from said biological sample, and analysing said DNA for the presence or absence or zygosity status of a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5.

Also provided is a method for the identification and/or selection of a cereal (e.g. wheat) plant comprising a functional restorer gene allele for wheat G-type cytoplasmic male sterility comprising the steps of
   a. identifying or detecting in said plant the presence of the nucleic acid having a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5 or the polypeptide comprising an amino acid sequence substantially identical to SEQ ID NO: 5;
   b. and optionally selecting said plant comprising said nucleic acid or polypeptide.

Likewise, identifying or detecting can involve obtaining a biological sample (e.g. protein) or genomic DNA and determining the presence of the nucleic acid or polypeptide according to methods well known in the art, such as hybridization, PCR, Rt-PCR, Southern blotting, Southern-by-sequencing, SNP detection methods (e.g. as described herein), western blotting, ELISA, etc. based on the sequences provided herein.

The invention also provides the use of the sequence(s) of the functional restorer gene for wheat G-type cytoplasmic male sterility located on chromosome 1A for the identification of at least one further marker comprising an allele linked to said functional restorer gene for wheat G-type cytoplasmic male sterility located on chromosome 1A. Such markers are also genetically linked or tightly linked to the restorer gene, and are also within the scope of the invention. Markers can be identified by any of a variety of genetic or physical mapping techniques. Methods of determining whether markers are genetically linked to a restorer gene are known to those of skill in the art and include, for example, interval mapping (Lander and Botstein, (1989) Genetics 121:185), regression mapping (Haley and Knott, (1992) Heredity 69:315) or MQM mapping (Jansen, (1994) Genetics 138:871), rMQM mapping. In addition, such physical mapping techniques as chromosome walking, contig mapping and assembly, amplicon resequencing, transcriptome sequencing, targeted capture and sequencing, next generation sequencing and the like, can be employed to identify and isolate additional sequences useful as markers in the context of the present invention.

The invention further provides the use of a nucleotide sequence substantially identical to SEQ ID NO: 4 from nucleotide position 55 to nucleotide position 2433, or a nucleotide sequence encoding a polypeptide comprising an amino acid sequence substantially identical to SEQ ID NO: 5, or the use of a polypeptide substantially identical to the amino acid sequence of SEQ ID NO: 5 for the identification of a plant comprising said functional restorer gene for wheat G-type cytoplasmic male sterility or for producing hybrid seed.

Also provided is the use of a plant obtained by any of the methods as described herein and comprising at least one marker allele linked to a functional restorer gene for wheat G-type cytoplasmic male sterility located on chromosome 1A as described herein, for restoring fertility in a progeny of a G-type cytoplasmic male sterile cereal plant, such as a wheat plant, or for producing a population of hybrid cereal plants, such as wheat plants.

Further provided is a recombinant nucleic acid molecule, especially a recombinant DNA molecule, which comprises a functional restorer gene as described herein. In one embodiment the recombinant DNA molecule comprises a plant expressible promoter, preferably a heterologous plant promoter, operably linked to a nucleotide sequence having substantial identity as herein defined to a nucleotide sequence of SEQ ID NO: 4 from nucleotide position 55 to nucleotide position 2433, or to the nucleotide sequence of SEQ ID NO: 4, or encoding a polypeptide comprising an amino acid sequence substantially identical to the amino acid sequence of SEQ ID NO: 5. The recombinant DNA molecule may optionally comprise a transcription termination and polyadenylation region, preferably functional in plant cells. Also, a DNA vector is provided comprising the recombinant DNA. The recombinant DNA molecule or DNA vector may be an isolated or modified nucleic acid molecule. The DNA comprising the functional restorer gene may be in a microorganism, such as a bacterium (e.g. *Agrobacterium* or *E. coli*).

The term "heterologous" refers to the relationship between two or more nucleic acid or protein sequences that are derived from different sources. For example, a promoter is heterologous with respect to an operably linked nucleic acid sequence, such as a coding sequence, if such a combination is not normally found in nature. In addition, a particular sequence may be "heterologous" with respect to a cell or organism into which it is inserted (i.e. does not naturally occur in that particular cell or organism). In one embodiment the term "heterologous" as used herein when referring to a nucleic acid or protein occurring in a certain plant species, also includes a nucleic acid or protein whose sequence has been modified or mutated compared to the previously existing nucleic acid or protein sequence occurring in said plant species. Hence, after the deletion, addition or substitution of one or more nucleotides in a nucleic acid or one or more amino acids in a protein sequence occurring in a wheat plant (e.g., modifying a native promoter to include regulatory elements that increase transcription, such as an enhancer element, or modifying a native promoter by inactivating or removing certain negative regulatory elements, such as repressor elements or target sites for miRNAs or lncRNAs), such a modified nucleic acid or protein is also considered heterologous to the wheat plant or to the operably-linked sequences.

The functional restorer gene allele can also encode a PPR protein having a mutation in an α-helical domain of a PPR motif, such as a mutation that affects hairpin formation between two of the α-helices making up a PPR motif.

The functional restorer gene allele can also encode a PPR protein having a mutation that affects dimerization of the PPR protein. It has e.g. been found that 'Thylakoid assembly 8' (THA8) protein is a pentatricopeptide repeat (PPR) RNA-binding protein required for the splicing of the transcript of ycf3, a gene involved in chloroplast thylakoid-membrane biogenesis. THA8 forms an asymmetric dimer once bound to single stranded RNA, with the bound RNA at the dimer interface. This dimer complex formation is mediated by the N-terminal PPR motifs 1 and 2 and the C-terminal motifs 4 and 5 (Ke et al., 2013, Nature Structural & Molecular Biology, 20, 1377-1382).

The functional restorer gene allele can also encode a PPR protein which when expressed is targeted to the mitochondrion or other organelle. This can e.g. be accomplished by the presence of a (plant-functional) mitochondrial targeting sequence or mitochondrial signal peptide, or mitochondrial transit peptide or other organelle targeting signal. A mitochondrial targeting signal is a 10-70 amino acid long peptide that directs a newly synthesized protein to the mitochondria, typically found at the N-terminus. Mitochondrial transit peptides are rich in positively charged amino acids but usually lack negative charges. They have the potential to form amphipathic α-helices in non-aqueous environments, such as membranes. Mitochondrial targeting signals can contain additional signals that subsequently target the protein to different regions of the mitochondria, such as the mitochondrial matrix. Like signal peptides, mitochondrial targeting signals are cleaved once targeting is complete. Mitochondrial transit peptides are e.g. described in Shewry and Gutteridge (1992, Plant Protein Engineering, 143-146, and references therein), Sjoling and Glaser (Trends Plant Sci Volume 3, Issue 4, 1 Apr. 1998, Pages 136-140), Pfanner (2000, Current Biol, Volume 10, Issue 11, pages R412-R415), Huang et al (2009, Plant Phys 150(3): 1272-1285), Chen et al. (1996, PNAS, Vol. 93, pp. 11763-11768), Fujii et al. (Plant J 2016, 86, 504-513). The amino acid sequence of SEQ ID NO: 5 from position 1 to position 48 is an example of such mitochondrial targeting sequence.

In a further embodiment, said functional restorer gene allele encoded by said (isolated) nucleic acid molecule is obtainable from USDA accession number PI 583676.

Also provided is a(n) (isolated or modified) polypeptide encoded by the nucleic acid molecule as described above, the polypeptide being a functional restorer protein for wheat G-type cytoplasmic male sterility, or comprising an amino acid sequence substantially identical to the amino acid sequence of SEQ ID NO: 5.

The functional restorer gene allele may also be cloned and a chimeric gene may be made, e.g. by operably linking a plant expressible promoter to the functional restorer gene allele and optionally a 3' end region involved in transcription termination and polyadenylation functional in plants. Such a chimeric gene may be introduced into a plant cell, and the plant cell may be regenerated into a whole plant to produce a transgenic plant. In one aspect the transgenic plant is a cereal plant, such as a wheat plant, according to any method well known in the art.

Thus, in a particular embodiment a chimeric gene is provided comprising a(n) (isolated or modified) nucleic acid molecule encoding the functional restorer gene allele as described above, operably linked to a heterologous plant-expressible promoter and optionally a 3' termination and polyadenylation region.

The use of such a (isolated or extracted or modified) nucleic acid molecule and/or of such a chimeric gene and/or of such a chromosome fragment for generating plant cells and plants comprising a functional restorer gene allele is encompassed herein. In one aspect it may be used to generate transgenic cereal (e.g. wheat) cells, plants and plant parts or seeds comprising the functional restorer gene allele and the plant having the capacity to restore fertility against wheat G-type cytoplasmic male sterility as described above.

A host or host cell, such as a (cereal) plant cell or (cereal) plant or seed thereof, such as a wheat plant cell or plant or seed thereof, comprising the (isolated or modified) nucleic acid molecule, (isolated or modified) polypeptide, or the chimeric gene as described above is provided, wherein preferably said polypeptide, said nucleic acid, or said chimeric gene in each case is heterologous with respect to said plant cell or plant or seed, or is modified. The host cell can also be a bacterium, such as *E. coli* or *Agrobacterium* sp. such as *A. tumefaciens*.

Thus, also provided is a method for producing a cereal plant cell or plant or seed thereof, such as a wheat plant cell or plant or seed thereof, comprising a functional restorer gene for wheat G-type cytoplasmic male sterility, or a method for increasing restoration capacity for wheat G-type cytoplasmic male sterility ("CMS") in a cereal plant, such as a wheat plant, comprising the steps of providing said plant cell or plant with the isolated or modified nucleic acid molecule, or the chimeric gene as described herein wherein said providing comprises transformation, crossing, backcrossing, genome editing or mutagenesis. Restoration capacity, as used herein, means the capacity of a plant to restore fertility in the progeny of a cross with a G-type cytoplasmic male sterility line. Preferably, said plant expresses or has increased expression of the polypeptide according to the invention. Preferably, said (increase in) expression is at least during (the early phases of) pollen development and meiosis, such as in anther or, more specifically, tapetum, or developing microspores (where said plant did not express or to a lesser extent expressed the polypeptide prior to the providing step).

Thus, also provided is a method for producing a cereal plant cell or plant or seed thereof, such as a wheat plant cell or plant or seed thereof, with restoration capacity for wheat G-type cytoplasmic male sterility, or a method for increasing restoration capacity for wheat G-type cytoplasmic male sterility in a cereal plant, such as a wheat plant, comprising the steps of increasing the expression of the (isolated or modified) polypeptide as described herein in said plant cell or plant or seed. Preferably, said (increase in) expression is at least during (the early phases of) pollen development and meiosis, such as in anther or, more specifically, tapetum, or developing microspores. Prior to the expression step or the increasing of expression step, said plant did not express or to a lesser extent expressed the polypeptide and/or did not have or to a lesser extent had restoration capacity for wheat G-type cytoplasmic male sterility. In one embodiment, the expression of the polypeptide as described herein is increased by engineering the nucleotide sequence encoding the restorer polypeptide, including by deliberate modification of the nucleotide sequence of the gene encoding the restorer polypeptide, such as increasing gene copy number of the gene, inserting modifications that increase stability of the RNA transcribed from the gene or of the polypeptide expressed from the gene, modifications of the upstream region/promoter region, modifications of the transcription termination and polyadenylation region etc.

Increasing the expression can be done by providing the plant with the (recombinant) chromosome fragment or the (isolated or modified) nucleic acid molecule or the chimeric gene as described herein, whereby the nucleic acid encoding the functional restorer gene allele is under the control of appropriate regulatory elements such as a promoter driving expression in the desired tissues/cells, but also by providing the plant with transcription factors that e.g. (specifically) recognise the promoter region and promote transcription, such as TAL effectors, dCas ("dead" Cas), dCpf1 ("dead" Cpf1) etc. coupled to transcriptional enhancers.

Further described is a method for converting a cereal plant, such as a wheat plant, not having the capacity to restore fertility in the progeny of a cross with a G-type cytoplasmic male sterility line (a non-restorer plant) into a plant having the capacity to restore fertility in the progeny of a cross with a G-type cytoplasmic male sterility line (a restorer plant), comprising the steps of modifying the genome of said plant to comprise (or to comprise and express) the (isolated or modified) nucleic acid molecule or the chimeric gene encoding a functional restorer gene allele for wheat G-type cytoplasmic male sterility as described herein wherein said modifying comprises transformation, crossing, backcrossing, genome editing or mutagenesis. preferably by transformation, genome editing or mutagenesis. Preferably, said plant expresses the polypeptide according to the invention, particularly at least during (the early phases of) pollen development and meiosis, such as in anther or, more specifically, tapetum, or developing microspores. Prior to said modification said plant did not express or to a lesser extent expressed the polypeptide and/or did not have or to a lesser extent had restoration capacity for wheat G-type cytoplasmic male sterility.

Also provided is a method for converting a non-restoring cereal plant, such as a wheat plant, into a restoring plant for wheat G-type cytoplasmic male sterility, or for increasing restoration capacity for wheat G-type cytoplasmic male sterility in a cereal plant, such as a wheat plant, comprising the steps of modifying the genome of said plant to increase the expression of a polypeptide according to the invention in said plant. Preferably, said (increase in) expression is at least during (the early phases of) pollen development and meiosis such as in anther or, more specifically, tapetum, or developing microspores. Prior to said modification said plant did not express or to a lesser extent expressed the polypeptide and/or did not have or to a lesser extent had restoration capacity for wheat G-type cytoplasmic male sterility.

Modifying the genome to increase expression of the polypeptide can for example be done by modifying the native promoter to include regulatory elements that increase transcription, such as certain enhancer element, but also by inactivating or removing certain negative regulatory elements, such as repressor elements or target sites for miRNAs or lncRNAs. The Rf1 5'upstream region including the promoter is included in SEQ ID NO 1 upstream of nucleotide 3616.

Also described is a plant cell or plant, preferably a cereal plant cell or cereal plant or seed thereof, such as a wheat plant cell or plant or seed thereof, produced according to any of the above methods, preferably wherein said plant has an increased restoration capacity for wheat G-type cytoplasmic male sterility compared to said plant prior to the providing step or the modification step. Use of such a plant obtained according to the above methods to restore fertility in the progeny of a cross with a G-type cytoplasmic male sterility plant or to produce hybrid plants or hybrid seed is also described. Such a plant cell, plant or seed can be a hybrid plant cell, plant or seed.

Genome editing, as used herein, refers to the targeted modification of genomic DNA using sequence-specific enzymes (such as endonuclease, nickases, base conversion enzymes) and/or donor nucleic acids (e.g. dsDNA, oligo's) to introduce desired changes in the DNA. Sequence-specific nucleases that can be programmed to recognize specific DNA sequences include meganucleases (MGNs), zinc-finger nucleases (ZFNs), TAL-effector nucleases (TALENs) and RNA-guided or DNA-guided nucleases such as Cas9, Cpf1, CasX, CasY, C2c1, C2c3, certain Argonaut-based systems (see e.g. Osakabe and Osakabe, Plant Cell Physiol. 2015 March; 56(3):389-400; Ma et al., Mol Plant. 2016 Jul. 6; 9(7):961-74; Bortesie et al., Plant Biotech J, 2016, 14; Murovec et al., Plant Biotechnol J. 15:917-926, 2017; Nakade et al., Bioengineered Vol 8, No. 3: 265-273, 2017; Burstein et al., Nature 542, 37-241; Komor et al., Nature 533, 420-424, 2016; all incorporated herein by reference). Donor nucleic acids can be used as a template for repair of the DNA break induced by a sequence specific nuclease, but can also be used as such for gene targeting (without DNA break induction) to introduce a desired change into the genomic DNA.

Accordingly, using these technologies, plants lacking a functional restorer gene for wheat G-type cytoplasmic male sterility (non-restoring plants) can be converted to restoring plants by making the desired changes to existing Rf-PPR genes or alternatively to introduce one or more complete sequences encoding functional Rf-PPR proteins, e.g. as described herein, at a specific genomic location.

Mutagenesis as used herein, refers to e.g. EMS mutagenesis or radiation induced mutagenesis and the like.

Transgenic cereal cells, e.g. transgenic wheat cells, comprising in their genome a(n) (isolated or modified) nucleic acid molecule as described or a chimeric gene as described comprising a functional restorer gene allele as described are also an embodiment of the invention. In one aspect the DNA molecule comprising Rf allele is stably integrated into the cereal (e.g. wheat) genome.

Thus, cereal plants, plant parts, plant cells, or seeds thereof, especially wheat, comprising a nucleic acid molecule according to the invention or a polypeptide according to the invention or a chimeric gene according to the invention encoding a functional restorer gene according to the invention, are provided, said plant having the capacity to restore fertility against wheat G-type cytoplasmic male sterility are provided herein. In one embodiment, the nucleic acid molecule, polypeptide or chimeric gene is heterologous to the plant, such as transgenic cereal plants or transgenic wheat plants. This also includes plant cells or cell cultures comprising such a nucleic acid molecule, polypeptide or chimeric gene, independent whether introduced by transgenic methods or by breeding methods. The cells are e.g. in vitro and are regenerable into plants comprising the chromosome fragment or nucleic acid molecule or chimeric gene of the invention. Said plants, plant parts, plant cells and seeds may also be hybrid plants, plant parts, plant cells or seeds.

Such plants may also be used as male parent plant in a method for producing F1 hybrid seeds or F1 hybrid plants, as described above.

A plant-expressible promoter as used herein can be any promoter that drives sufficient expression at least during (early) pollen development and meiosis, such as in anther, or more specifically in tapetum or developing microspore. This can for example be a constitutive promoter, an inducible promoter, but also a pollen-, anther-, tapetum- or microspore-specific/preferential promoter.

A constitutive promoter is a promoter capable of directing high levels of expression in most cell types (in a spatio-temporal independent manner). Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988, Mol. Gen. Genet. 212: 182-190) or 19S RNAs genes (Odell et al., 1985, Nature. 6; 313(6005):810-2; U.S. Pat. No. 5,352,605; WO 84/02913; Benfey et al., 1989, EMBO J. 8:2195-2202), the enhanced 2×35S promoter (Kay at al., 1987, Science 236:1299-1302; Datla et al. (1993), Plant Sci 94:139-149) promoters of the cassava vein mosaic virus (CsVMV; WO 97/48819, U.S. Pat. No. 7,053,205), 2×CsVMV (WO2004/053135) the circovirus (AU 689 311) promoter, the sugarcane baciliform badnavirus (ScBV) promoter (Samac et al., 2004, Transgenic Res. 13(4):349-61), the figwort mosaic virus (FMV) promoter (Sanger et al., 1990, Plant Mol Biol. 14(3):433-43), the subterranean clover virus promoter No 4 or No 7 (WO 96/06932) and the enhanced 35S promoter as described in U.S. Pat. Nos. 5,164,316, 5,196,525, 5,322,938, 5,359,142 and 5,424,200. Among the promoters of plant origin, mention will be made of the promoters of the plant ribulose-biscarboxylase/oxygenase (Rubisco) small subunit promoter (U.S. Pat. No. 4,962,028; WO99/25842) from *Zea mays* and sunflower, the promoter of the *Arabidopsis thaliana* histone H4 gene (Chabouté et al., Plant Mol. Biol. 8, 179-191, 1987), the ubiquitin promoters (Holtorf et al., 1995, Plant Mol. Biol. 29:637-649, U.S. Pat. No. 5,510,474) of Maize, Rice and sugarcane, the Rice actin 1 promoter (Act-1, U.S. Pat. No. 5,641,876), the histone promoters as described in EP 0 507 698 A1, the Maize alcohol dehydrogenase 1 promoter (Adh-1) (from http://www.patentlens.net/daisy/promoters/242.html)). Also the small subunit promoter from *Chrysanthemum* may be used if that use is combined with the use of the respective terminator (Outchkourov et al., Planta, 216: 1003-1012, 2003).

Examples of inducible promoters include promoters regulated by application of chemical compounds, including alcohol-regulated promoters (see e.g. EP637339), tetracycline regulated promoters (see e.g. U.S. Pat. No. 5,464,758), steroid-regulated promoters (see e.g. U.S. Pat. Nos. 5,512,483; 6,063,985; 6,784,340; 6,379,945; WO01/62780), metal-regulated promoters (see e.g. U.S. Pat. No. 4,601,978) but also developmentally regulated promoters.

Pollen/microspore-active promoters include e.g. a maize pollen specific promoter (see, e.g., Guerrero (1990) Mol. Gen. Genet. 224:161 168), PTA29, PTA26 and PTA13 (e.g., see U.S. Pat. No. 5,792,929) and as described in e.g. Baerson et al. (1994 Plant Mol. Biol. 26: 1947-1959), the NMT19 microspore-specific promoter as e.g. described in WO97/30166. Further anther/pollen-specific or anther/pollen-active promoters are described in e.g. Khurana et al., 2012 (Critical Reviews in Plant Sciences, 31: 359-390), WO2005100575, WO 2008037436. Other suitable promoters are e.g the barley vrn1 promoter, such as described in Alonso-Peral et al. (2001, PLoS One. 2011; 6(12):e29456).

Examples of tissue specific promoters include meristem specific promoters such as the rice OSH1 promoter (Sato et al. (1996) Proc. Natl. Acad. Sci. USA 93:8117-8122) rice metallothein promoter (BAD87835.1) WAK1 and WAK2 promoters (Wagner & Kohorn (2001) Plant Cell 13(2):

303-318, spike tissue specific promoter D5 from barley (U.S. Pat. No. 6,291,666), the lemma/palea specific Lem2 promoter from barley (Abebe et al. (2005) Planta, 221, 170-183), the early inflorescence specific Pvrn1 promoter from barley (Alonse Peral et al. 2011, PLoS ONE 6(12) e29456), the early inflorescence specific Pcrs4/PrA2 promoter from barley (Koppolu et al. 2013, Proc. Natl. Acad. Sci USA, 110(32), 13198-13203), the meristem specific pkn1 promoter with the Act1 intron from rice (Zhang et al., 1998, Planta 204: 542-549, Postma-Haarsma et al. 2002, Plant Molecular Biology 48: 423-441) the SAM/inflorescence specific promoter from Dendrobium sp. Pdomads1 (Yu et al. 2002, Plant Molecular Biology 49: 225-237).

It will be clear that the herein identified nucleic acids and polypeptides can be used to identify further functional restorer genes for wheat G-type cytoplasmic male sterility. Thus, the invention also provides the use of the isolated or modified nucleic acids or polypeptides as disclosed herein, such as SEQ ID 4, to identify one or more further functional restorer genes for wheat G-type cytoplasmic male sterility.

Further, homologous or substantially identical functional restorer genes can be identified using methods known in the art. Homologous nucleotide sequence may be identified and isolated by hybridization under stringent or high stringent conditions using as probes a nucleic acid comprising e.g. the nucleotide sequence of SEQ ID NO: 4 or part thereof, as described herein. Other sequences encoding functional restorer genes may also be obtained by DNA amplification using oligonucleotides specific for genes encoding functional restorer genes as primers, such as but not limited to oligonucleotides comprising or consisting of about 20 to about 50 consecutive nucleotides from SEQ ID NO: 4 or its complement. Homologous or substantially identical functional restorer genes can be identified in silico using Basic Local Alignment Search Tool (BLAST) homology search with the nucleotide or amino acid sequences as provided herein.

Functionality of restorer genes or alleles thereof, such as identified as above, can be validated for example by providing, e.g. by transformation or crossing, such a restorer gene under control of a plant-expressible promoter in a cereal (wheat) plant that does not have the capacity to restore fertility of offspring of a G-type cytoplasmic male sterile wheat plant, crossing the thus generated cereal plant with a G-type cytoplasmic male sterile wheat plant and evaluating seed set in the progeny. Alternatively, a restorer line can be transformed with an RNAi construct or gene-edited with e.g. CRISPR-Cas technology or any other sequence specific nuclease to generate a loss of function variant that renders the plant non-restoring. Similarly, other means for mutating the restorer gene (e.g. EMS, γ-radiation) can be used to evaluate the effect of a loss of function mutation on restoring ability.

In any of the herein described embodiments and aspects the plant may comprise or may be selected to comprise or may be provided with a further functional restorer gene for wheat G-type cytoplasmic male sterility (located on or obtainable from the same or another chromosome), such as Rf2 (7D), Rf3 (1B), Rf4 (6B), Rf5 (6D), R16 (5D), Rf7 (7B), R18, 6AS or 6BS (Tahir & Tsunewaki, 1969, supra; Yen et al., 1969, supra; Bahl & Maan, 1973, supra; Du et al., 1991, supra; Sihna et al., 2013, supra; Ma et al., 1991, supra; Zhou et al., 2005, supra).

Any of the herein described methods, markers and marker alleles, nucleic acids, polypeptides, chimeric genes, plants may also be used to restore fertility against $S^v$-type cytoplasm, as e.g. described in Ahmed et al 2001 (supra). The methods, nucleic acids, polypeptides, chimeric genes may also be useful to restore fertility against other male-sterility inducing germplasm in wheat or other cereals.

Definitions

As used herein a "chimeric gene" refers to a nucleic acid construct which is not normally found in a plant species. A chimeric nucleic acid construct can be DNA or RNA. "Chimeric DNA construct" and "chimeric gene" are used interchangeably to denote a gene in which the promoter or one or more other regulatory regions, such as a transcription termination and polyadenylation region of the gene are not associated in nature with part or all of the transcribed DNA region, or a gene which is present in a locus in the plant genome in which it does not occur naturally or present in a plant in which it does not naturally occur. In other words, the gene and the operably-linked regulatory region or the gene and the genomic locus or the gene and the plant are heterologous with respect to each other, i.e. they do not naturally occur together. This includes the situation wherein one or more of the regulatory elements (such as the promoter or the 3' end formation and polyadenylation region) or the coding region, of a wheat gene (such as the Rf1_PPR_09 gene of the current invention), is a modified nucleic acid (as that is not normally found in wheat, and is heterologous to the gene elements it is operably-linked to).

A first nucleotide sequence is "operably linked" with a second nucleic acid sequence when the first nucleic acid sequence is in a functional relationship with the second nucleic acid sequence. For example, a promoter is operably linked to a coding sequence if the promoter affects the transcription or expression of the coding sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

"Backcrossing" refers to a breeding method by which a (single) trait, such as fertility restoration (Rf), can be transferred from one genetic background (a "donor") into another genetic background (also referred to as "recurrent parent"), e.g. a plant not comprising such an Rf gene or locus. An offspring of a cross (e.g. an F1 plant obtained by crossing an Rf containing with an Rf lacking plant; or an F2 plant or F3 plant, etc., obtained from selfing the F1) is "backcrossed" to the parent. After repeated backcrossing (BC1, BC2, etc.) and optionally selfings (BC1S1, BC2S1, etc.), the trait of the one genetic background is incorporated into the other genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and physically linked to an Rf locus, can be used to detect and/or select plants comprising the Rf locus. The closer the genetic linkage of the molecular marker to the locus, the less likely it is that the marker is dissociated from the locus through meiotic recombination.

A "biological sample" can be a plant or part of a plant such as a plant tissue or a plant cell or an extract of a plant or part of a plant, including protein.

"Providing genomic DNA" as used herein refers to providing a sample comprising genomic DNA from the plant. The sample can refer to a tissue sample which has been obtained from said plant, such as, for example, a leaf sample, comprising genomic DNA from said plant. The sample can further refer to genomic DNA which is obtained from a tissue sample, such as genomic DNA which has been obtained from a tissue, such as a leaf sample. Providing genomic DNA can include, but does not need to include, purification of genomic DNA from the tissue sample. Providing genomic DNA thus also includes obtaining tissue material from a plant or larger piece of tissue and preparing a crude extract or lysate therefrom.

"Isolated DNA" or "isolated nucleic acid" as used herein refers to DNA or nucleic acid not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome. "Isolated", as used herein, when referring to a protein (sequence) also includes a protein (sequence) that has been modified by man (e.g., by modifying the nucleic acid encoding that protein) as is done in an effort to obtain some improvement of protein activity (such as restoration activity). "Isolated", as used herein, when referring to a nucleic acid (sequence) also includes a nucleic acid (sequence) that has been modified by man (e.g., by inserting, deleting or substituting one or more nucleotides in the native nucleic acid) as is done in an effort to obtain some improvement (like improvement in RNA or protein expression, targeting or stability, or improvement in protein activity (such as restoration activity)). A "modified" nucleic acid or protein (sequence), as used herein, refers to a nucleic acid or protein (sequence) that is different to the native nucleic acid or protein, by modifying or mutating the nucleic acid or protein (or the nucleic acid encoding the protein), as is done in an effort to obtain some improvement.

In one embodiment of the invention, a Rf1_PPR_09 nucleic acid has a modified or mutated sequence compared to the sequence in SEQ ID No. 1 or 4, wherein the nucleotide at a position corresponding to nucleotide position 3286 in SEQ ID No. 1 (or the nucleotide at a position corresponding to nucleotide position 2286 in SEQ ID No. 4) is a G, or has a modified or mutated sequence compared to the sequence in SEQ ID No. 1, wherein said modified or mutated sequence has a stretch of at most 6 A's, preferably 6 A's, between the T corresponding to the nucleotide position 753 in SEQ ID NO: 1 and the C corresponding to the nucleotide position 760 in SEQ ID NO: 1. In one embodiment of the invention, a Rf1_PPR_09 nucleic acid has a modified or mutated sequence compared to the sequence in SEQ ID No. 1, wherein the nucleotide at a position corresponding to nucleotide position 3286 in SEQ ID No. 1 is a G, and wherein said modified or mutated sequence has a stretch of at most 6 A's, preferably 6 A's, between the T corresponding to the nucleotide position 753 in SEQ ID NO: 1 and the C corresponding to the nucleotide position 760 in SEQ ID NO: 1. In one embodiment, a modified or mutated nucleic acid of SEQ ID NO:1 from nucleotide positon 1 to nucleotide position 1054, comprises a stretch of at most 6 A's, preferably 6 A's, between the T corresponding to the nucleotide position 753 in SEQ ID NO: 1 and the C corresponding to the nucleotide position 760 in SEQ ID NO: 1. In one embodiment, such a modified or mutated Rf1_PPR_09 nucleic acid encodes a modified Rf1_PPR_09 protein having a modified or mutated amino acid sequence when compared to the sequence shown in SEQ ID No. 5.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the restoring capacity), such as seed obtained by selfing or crossing, e.g. hybrid seed (obtained by crossing two inbred parental lines), hybrid plants and plant parts derived there from are encompassed herein, unless otherwise indicated. In some embodiments, the plant cells of the invention may be non-propagating cells.

The obtained plants according to the invention can be used in a conventional breeding scheme to produce more plants with the same characteristics or to introduce the characteristic of the presence of the restorer gene according to the invention in other varieties of the same or related plant species, or in hybrid plants. The obtained plants can further be used for creating propagating material. Plants according to the invention can further be used to produce gametes, seeds, flour, embryos, either zygotic or somatic, progeny or hybrids of plants obtained by methods of the invention. Seeds obtained from the plants according to the invention are also encompassed by the invention.

"Creating propagating material", as used herein, relates to any means known in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Transformation, as used herein, means introducing a nucleotide sequence into a plant in a manner to cause stable or transient expression of the sequence. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

As used herein, the term "homologous" or "substantially identical" or "substantially similar" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence (e.g., SEQ ID NO: 1 or 4). In one embodiment, a nucleic acid sequence substantially identical or substantially similar to SEQ ID NO: 4 (or SEQ ID NO: 4 from nucleotide position 55 to nucleotide position 2433) is more than 85%; 86%; 87%; 88%; 89%; 90%; 91%; 92%; 93%; 94%; 95%;

96%; 97%; 98%; 99% or more than 99.5% identical to SEQ ID NO:4 (or SEQ ID NO: 4 from nucleotide position 55 to 2433), and has a G nucleotide at the nucleotide position corresponding to the nucleotide position 2286 in SEQ ID NO: 4. In one embodiment, a nucleic acid sequence substantially identical or substantially similar to SEQ ID NO: 1 (or SEQ ID NO: 1 from nucleotide position 1055 to nucleotide position 3433) is more than 85%; 86%; 87%; 88%; 89%; 90%; 91%; 92%; 93%; 94%; 95%; 96%; 97%; 98%; 99% or more than 99.5% identical to SEQ ID NO:1 (or SEQ ID NO: 1 from nucleotide position 1055 to 3433), and has a G nucleotide at the nucleotide position corresponding to the nucleotide position 3286 in SEQ ID NO: 1, or has a stretch of at most 6 A's, preferably 6 A's, between the T corresponding to the nucleotide position 753 in SEQ ID NO: 1 and the C corresponding to the nucleotide position 760 in SEQ ID NO: 1. In one embodiment, a nucleic acid sequence substantially identical or substantially similar to SEQ ID NO: 1 (or SEQ ID NO: 1 from nucleotide position 1055 to nucleotide position 3433) is more than 85%; 86%; 87%; 88%; 89%; 90%; 91%; 92%; 93%; 94%; 95%; 96%; 97%; 98%; 99% or more than 99.5% identical to SEQ ID NO:1 (or SEQ ID NO: 1 from nucleotide position 1055 to 3433), and has a G nucleotide at the nucleotide position corresponding to the nucleotide position 3286 in SEQ ID NO: 1, and has a stretch of at most 6 A's between the T corresponding to the nucleotide position 753 in SEQ ID NO: 1 and the C corresponding to the nucleotide position 760 in SEQ ID NO: 1. In one embodiment, included in the invention is a nucleic acid sequence substantially identical or substantially similar to SEQ ID NO: 1 from nucleotide position 1 to nucleotide position 1054, wherein said nucleic acid sequence is more than 85%; 86%; 87%; 88%; 89%; 90%; 91%; 92%; 93%; 94%; 95%; 96%; 97%; 98%; 99% or more than 99.5% identical to SEQ ID NO:1 from nucleotide position 1 to 1054, and has a stretch of at most 6 A's, preferably 6 A's, between the T corresponding to the nucleotide position 753 in SEQ ID NO: 1 and the C corresponding to the nucleotide position 760 in SEQ ID NO: 1. A probe may also be a nucleic acid molecule that is "specifically hybridizable" or "specifically complementary" to an exact copy of the marker to be detected ("DNA target"). "Specifically hybridizable" or "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions, preferably highly stringent conditions.

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 μg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989, Molecular Cloning: A Laboratory Manual, Second Edition, Cold Spring Harbor Laboratory Press, NY) and Sambrook and Russell (2001, Molecular Cloning: A Laboratory Manual, Third Edition, Cold Spring Harbor Laboratory Press, NY).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

As used herein "exogenous" means having an external origin or cause, as opposed to "endogenous". An exogenous nucleic acid molecule is a nucleic acid molecule that does not naturally occur within the organism, and has been (historically) introduced or engineered to occur in an organism.

In certain jurisdictions, plants according to the invention, which however have been obtained exclusively by essentially biological processes, wherein a process for the production of plants is considered essentially biological if it consists entirely of natural phenomena such as crossing or selection, may be excluded from patentability. Plants according to the invention thus also encompass those plants not exclusively obtained by essentially biological processes.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The sequence listing contained in the file named "BCS18-2006_ST25.txt", which is 34 kilobytes (size as measured in Microsoft Windows®), contains 7 sequences SEQ ID NO: 1 through SEQ ID NO: 7, is filed herewith by electronic submission and is incorporated by reference herein.

The invention will be further described with reference to the examples described herein; however, it is to be understood that the invention is not limited to such examples.

Throughout the description reference is made to the following sequences

SEQ ID NO: 1: sequence of the genomic region from PI 583676 comprising the Rf1-PPR-09 gene
   Nt 1-1000: genomic region upstream of cDNA/mRNA transcript of Rf1-PPR-09
   Nt 1001-1054: 5'UTR
   Nt 1055-3433: CDS
   Nt 3434-3956: 3'UTR part 1
   Nt 4827-4919: 3'UTR part 2
   Nt 5398-5515: 3' UTR part 3
   Nt 5662-5708: 3' UTR part 4
   Nt 5854-6466: 3' UTR part 5
   Nt 6467-7923: genomic region downstream of cDNA/mRNA transcript of Rf1-PPR-09
SEQ ID NO: 2: ORF256 nucleotide sequence
SEQ ID NO: 3: predicted target sequence within ORF256
SEQ ID NO: 4: cDNA/mRNA Rf1-PPR-09
   Nt 1-54: 5'UTR
   Nt 55-2433: CDS
   Nt 2434-3827: 3'UTR
SEQ ID NO: 5: amino acid sequence Rf1-PPR-09
SEQ ID NO: 6: Forward primer (qPCR)
SEQ ID NO: 7: Reverse primer (qPCR)

EXAMPLES

Example 1—Plant Materials and Genetic Mapping

The Rf1 QTL was mapped on Chromosome 1A as described extensively in Examples 1 to 3 of WO2017158126 (herein incorporated by reference). Briefly, a male sterile line carrying *Triticum timopheevii* CMS, CMS005, and a male sterile restorer line responding to *Triticum timopheevii* CMS (*T. timopheevii* /2* lowin //2* Quivira, Accession number PI 583676, USDA National Small Grains Collection, also known as Dekalb 582M and registered as US PVP 7400045, available via the National Plant Germplasm System https://npgsweb.ars-grin.gov/gringlobal/accessiondetail.aspx?id=1478647), were used as parents to generate mapping population. A genetic map with total of 2080 SNP markers was established and covered all chromosomes of the wheat genome. The chromosome 1A was described by 108 SNP markers. QTL analysis was carried out using Haley-Knott regression to test the effect of variation in seed set across all markers. An interval of significantly associated markers was delineated, including left and right flanking markers (SEQ ID NO. 2 and SEQ ID NO. 4 of WO2017158126). The marker with the highest significance and biggest effect on restoration is the peak marker of SEQ ID NO. 3 of WO2017158126. This delimited the interval to 15.6 cM by the left and right flanking markers. For further fine-mapping, 40 F2 individuals that were heterozygous in the QTL region were selected based on phenotype and genotype. A total of 2560 individual F3 plants were grown in the field at 2 locations. For each plant, seed set on the main head under a bag was measured. Additional SNP assays were developed to increase the marker density in the QTL interval. A total of 361 additional SNP markers were using in mapping the 1A region. The Rf1 locus could be further delimited to a region of about 1.9 cM (from 30.9 to 32.8 cM along chromosome 1A).

Example 2—BAC Libraries of Restorer Line

A BAC library was constructed for the wheat restorer line referred to as Rf line 'PI 583676', by digesting high-molecular weight 'PI 583676' gDNA with a restriction enzyme, and transforming the resultant fragments (mean insert size ~80-130 Kb), into *E. coli*. The fine-mapping SNP marker sequences, or markers developed from the corresponding Rf region on the 'Chinese Spring' reference genome, were then used to design PCR primers to screen the pooled BAC clones. Once PCR-positive BAC pools had been identified, BACs from the pool were individualized and screened again with the same marker. Individual, PCR-positive BACs were then subjected to BAC-end sequencing to confirm integrity and the presence of the screening marker sequences. Finally verified positive BACs were deep sequenced using PacBio technology and reads assembled to generate a consensus sequence for the BAC insert. Sequenced, positive BACs were then aligned either by de novo assembly, or by assembly to the reference genome or tiled using the screening markers to generate a new 'PI 583676' reference sequence for the Rf1 QTL region. The 'PI 583676' Rf1 QTL reference sequence was then structurally and functionally annotated to identify any structural changes and/or differences in gene content and/or polymorphisms in the candidate gene captured within the region relative to the (non-restorer) reference genome. Structural annotation of the BACs assembled across the Rf1 QTL region using ab initio gene annotation programs, as well as by alignment of wheat EST sequences, wheat full-length cDNA sequences, wheat gene models and known restorer genes from orthologous species available from public databases. Functional annotation of genes in the QTL region was carried out using Blast2GO and PLAZA software programs as well as consultation of published literature. These candidate genes were then prioritized on the basis of their predicted functionality, the presence of polymorphisms relative to orthologous alleles in non-restoring lines and their homology to known Rf genes (Chen and Liu 2014, Annu. Rev. Plant Biol. 65 579-606; Dahan and Mireau 2013, RNA Biol. 10, 1469-1476).

The 'PI 583676' BAC library was screened multiple times using PCR markers developed from fine-mapping markers, reference genomes or isolated BAC sequences These BACs were sequenced individually. The sequenced BACs were found to contain the Rf-Rf1-PPR-09 gene herein described. These BACs represent the unique 'PI 583676' genome sequence for the Rf1 QTL region.

In line with the recent notion of Geyer et al. (2017, supra) that the Rf1 locus is likely of *T. timopheevii* origin, the Rf-PPR-09 gene is not present in the Chinese Spring reference genome.

As shown in FIG. 1 A, the gene structure for Rf1-Rf-PPR-09 is consisting of a single exon. This relatively simple gene structure appears to be typical for Rf-PPRs.

SEQ ID NO: 1 represents the genomic DNA sequence comprising the Rf1-PPR-09 gene.

Example 3—Annotation of the RF1-PPR-09 Amino Acid Sequence

Known Rf-PPRs are members of the P-class of PPR proteins, and contain up to −30 PPR motifs per protein, with each motif comprising 35 amino acids (Gaborieau, Brown, and Mireau 2016, Front. Plant Sci. 7, 1816). Structurally PPR proteins consist of 2 α-helices that form a hairpin and a super-groove, and it is this super groove that interacts with an RNA molecule. The amino acid composition of the individual PPR motifs determines RNA which nucleotide is recognized, and the number of PPR motifs determines the length of the RNA sequence on the target transcript. Here the Rf1-PPR-09 was annotated to identify PPR motifs and other sequence features and the results are summarized in FIGS. 1B and C.

Rf1-PPR-09 consists of 792 amino acids and contains 18 consecutive 35 amino-acid PPR motifs, and a predicted transit peptide that targets the protein to the mitochondria (SEQ ID NO: 5)—this was predicted by PredSL (Evangelia et al. (2006) Geno. Prot. Bio Info Vol 4, No. 1, 48-55), with a (strong) mTP (mitochondrial targeting peptide) score of 0.999741 in PredSL). This is very similar to the structure of the Rf-1A gene cloned from rice, which is 791 amino acids long and contains 16 Rf-PPR repeats (Akagi et al. 2004, Theor. Appl. Genet. 108, 1449-1457; Komori et al. 2004, Plant J. 37, 315-325).

Each PPR motif consists of 2 antiparallel helices that form a hairpin structure that interacts with a single stranded RNA molecule. Studies have demonstrated the existence of a recognition code linking the identity of specific amino acids within the repeats and the target RNA sequence of the PPR protein studied (Barkan et al. 2012, supra; Yagi et al. 2013, supra). (Barkan and Small 2014, supra). In particular the identity of the 2nd, 5th and the 35th amino acids of each motif have been shown to be particularly important. On the basis of the identity of the amino acids at positions 2, 5 and 35 in the PPR motif, the target transcript sequence for Rf1-PPR-09 protein can be predicted using a probability matrix table as described by Yagi et al 2013, supra. Following the PPR code, the predicted RNA target sequence on orf256 is ATTTCTCAAATAAAAA (SEQ ID No. 3), which can be found in the orf256 mRNA comprising the nucleotide sequence at positions 105 to 121 nucleotides downstream of the ATG start codon of orf256 (SEQ ID No.:2 from nucleotide 192 to nucleotide 207).

Example 4—Gene Expression and Link to Fertility Restoration in an Independent Population The link between Rf1-PPR-09 gene expression with fertility was tested in near-isogenic lines developed from a 16-way MAGIC population. This population was developed by intercrossing 16 founder lines, among which there were one line with cytoplasmic male sterility derived from *T. timopheevii* and two potential restorer lines, called R1 and R2. The 16-way MAGIC population was intercrossed for 5 generations and subsequently fixed through single-seed descent to F5. Throughout the line-fixation process, lines were genotyped and phenotyped for fertility. This allowed for the selection of families segregating for restoration as well as for additional fine mapping of the Rf loci. At F5, individuals with heterozygosity at the previously mapped Rf1 locus were identified and used to create multiple near-isogenic line (NIL) pairs with and without the Rf1 locus in their progeny. Six such NIL pairs were selected, grown, and phenotyped. RNAseq and qPCR experiments were performed on developmental spikes at 3 stages from six NIL pairs and also the respective parental lines using the primers of Table 1 (SEQ ID NOs: 6 and 7). Bioinformatic analysis of the RNAseq data allowed the identification of differentially expressed transcripts between restorer and non-restorer genotypes. The identified transcripts mapped into the QTL regions, had the correct (restoring) founder line.

TABLE 1

Primer sequences used for the gene expression analysis

| Gene i.d. | Name | Type | Target Region (SEQ ID NO. 1) | Sequence 5' → 3' | SEQ ID NO. |
|---|---|---|---|---|---|
| Rf1-PPR-9 | Fw1 | Primer | 3843-3862 | CTAAGGGTCAGAGTAATCAG | 6 |
|  | Rev1 | Primer | 3924-3943 complement | TGATGAGAACAAACCGGTCA | 7 |

Figure 2:
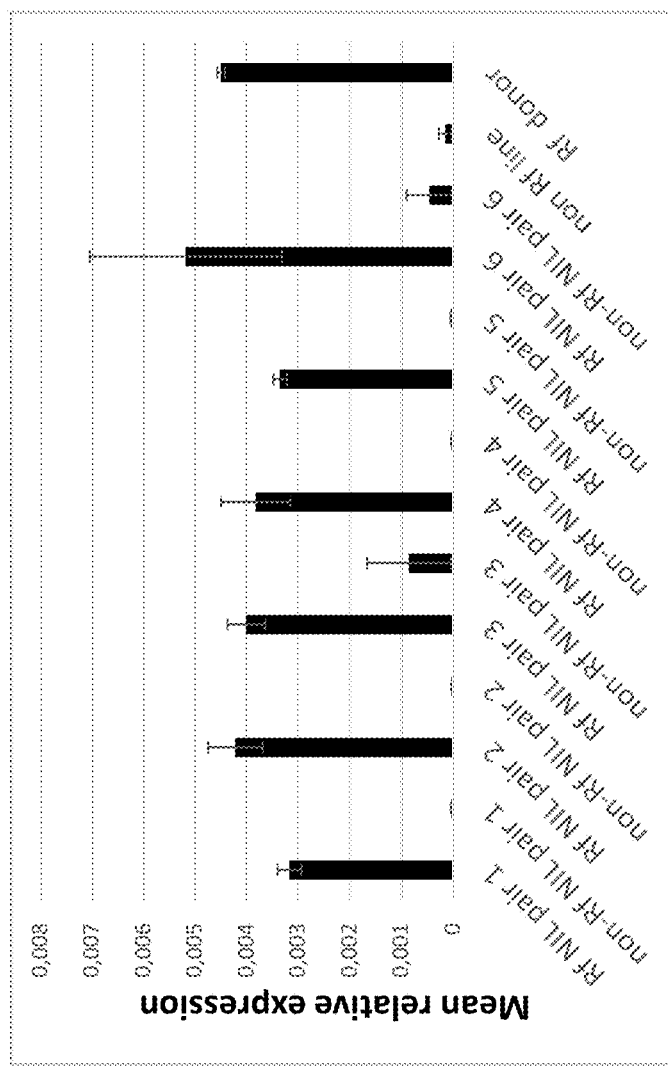
FIG. 2: Mean Relative Expression levels of Rf1-PPR-09 gene across 6 contrasting NIL pairs each with/without the Rf1 locus, as well as in a control line not containing the Rf1 locus and in Rf1 donor line. Rf1-containing progeny were identified following KASP genotyping with fine-mapping markers and phenotyped to confirm restoration of fertility.

As shown in FIG. 2, expression was exclusively found in the Rf donor line and in the Rf containing NILs in developing spikes of 3.5 cm length. Neither the non-Rf parent nor the wild-type segregants showed expression.

Example 5—Gene Validation

By Mutagenesis

A mutagenized population of the restorer line is constructed by EMS mutagenesis. Based on sequencing of the region around the Rf1-PPR-09 gene, mutant plants with an inactivating mutation in the Rf1-PPR-09 gene are identified. The homozygous mutant plants and their wildtype segregants are screened for fertility restoration capacity. The plants that have an inactivating mutant Rf1-PPR-09 gene no longer has restoring ability, confirming that the identified Rf1-PPR-09 gene is a functional Rf gene.

By Overexpression

The coding sequence of the Rf1-PPR-09 gene was cloned under the control of a constitutive UBIQUITIN promoter (pUbiZm) from maize, in a T-DNA expression vector comprising the bar selectable marker gene. The resulting vector was used to transform the transformable wheat variety Fielder, having no restoration capacity, according to methods well known in the art for wheat transformation (see e.g. Ishida et al Methods Mol Biol. 2015; 1223:189-98). The copy number of the transgene in the transgenic plant was determined by real time PCR on the selectable marker gene. The transformed plants comprising a single copy of the Rf1-PPR-09 gene cassette were transferred to the greenhouse. Transgenic T0 plants were crossed as male parents to a G-type cytoplasmic male sterile wheat line. F1 progeny of 15 events were grown for evaluation of restoration of seed production. All F1 progeny plants contain the G-type cytoplasm and segregate 1:1 (hemizygous:azygous) for presence of the Rf1-PPR-09 transgene locus. Expression of the transgene in leaf tissue and in young developing spikes of F1 plants was tested by qRT-PCR.

Pollen viability was evaluated by iodine staining for 3 azygous and 3 hemizygous plants per event and seed set was recorded on all spikes of up to 5 azygous and up to 5 hemizygous plants per event. The results show strong restoration of fertility in 5 events, moderate restoration of fertility in 3 events and weak or very weak restoration of fertility in 2 events, while 5 events did not show statistically significant restoration of seed set. Restoration of seed set strongly correlated with the frequency of pollen staining. Table 2 below shows the results for all events showing a statistically significant difference between seed set in azygous and hemizygous plants (using t-Test, two-sample, assuming unequal variances). Hemizygous plants could be divided in three groups for mRNA expression of the Rf1-PPR-09 transgene. All plants in the lowest expression group showed no, or very low seed set, while all plants in the highest expression group showed good seed set. Plants in the intermediate expression group showed diverse levels of seed set.

Hence, expression of the Rf1-PPR-09 gene restores fertility of G-type cytoplasmic male sterile wheat plants.

By Targeted Knock-Out

Guide RNAs for CRISPR-mediated gene editing targeting the mRNA coding sequence, preferably the protein coding sequence of the Rf1-PPR-09 gene, or the immediately upstream promoter sequence of the Rf1-PPR-09 gene are designed by using e.g. the CAS-finder tool. Preferably four unique or near-unique guide RNAs are designed per target gene. The guide RNAs are tested for targeting efficiency by PEG-mediated transient co-delivery of the gRNA expression vector with an expression vector for the respective nuclease, e.g. Cas9 or Cpf1, under control of appropriate promoters, to protoplasts of a wheat restorer line containing the Rf1-PPR-09 gene, preferably the line designated as *T. timopheevii* USDA Accession number PI 583676. Genomic DNA is extracted from the protoplasts after delivery of the guide RNA and nuclease vectors. After PCR amplification, integrity of the targeted Rf1-PPR-09 gene sequence is assessed by sequencing.

The one or two most efficient guide RNAs are used for stable gene editing in same wheat restorer line also containing the G-type CMS cytoplasm. For this purpose, the selected guide RNA expression vector, together with a nuclease expression module and a selectable marker gene, are introduced into embryos isolated from the before mentioned wheat restorer line using e.g. particle gun bombardment. Transgenic plants showing resistance to the selection agent are regenerated using methods known to those skilled in the art. Transgenic T0 plants containing gene targeting events, preferably small deletions resulting in a non-functional Rf1-PPR-09 gene are identified by PCR amplification and sequencing.

Transgenic T0 plants containing the G-type CMS cytoplasm and likely to contain a functional knock-out of the Rf1-PPR-09 gene, preferably in homozygous state, but alternatively in heterozygous state, are crossed as female parents to a spring wheat line with normal cytoplasm and without PPR-Rf genes. The F1 progeny of the crosses contains the G-type "CMS" cytoplasm and 50% (in case of heterozygous T0) or 100% (in case of homozygous T0) of the F1 progeny will lack a functional version of the target Rf-PPR gene. The F1 plants lacking a functional target Rf-PPR gene are identified using genomic PCR assays. The F1 plants show partial or complete loss of male fertility due to the knock-out of the Rf1-PPR-09 gene.

The level of male fertility in the F1 progeny lacking a functional version of the Rf1-PPR-07 gene is tested using four different assays. In the first assay the mitochondrial

TABLE 2

Restoration of G-type CMS in wheat by overexpression of Rf1-PPR-09

| | Azygous | | | Hemizygous | | | | |
| --- | --- | --- | --- | --- | --- | --- | --- | --- |
| Events | # plants | avg # seed | stdev # seed | # plants | avg # seed | stdev # seed | Restoring capacity | P-value (two-tail)* |
| Event 1 | 5 | 5.20 | 6.42 | 5 | 199.60 | 61.61 | strong | 0.002172185 |
| Event 2 | 5 | 0.00 | 0.00 | 5 | 226.20 | 34.95 | strong | 0.000132577 |
| Event 3 | 5 | 0.20 | 0.45 | 5 | 91.40 | 51.40 | moderate | 0.016578945 |
| Event 4 | 5 | 0.20 | 0.45 | 5 | 129.80 | 26.89 | moderate | 0.000420738 |
| Event 5 | 5 | 0.00 | 0.00 | 5 | 244.40 | 38.28 | strong | 0.000139825 |
| Event 6 | 5 | 0.60 | 0.89 | 5 | 238.60 | 27.72 | strong | 4.34558E−05 |
| Event 7 | 5 | 6.00 | 6.60 | 5 | 130.60 | 22.91 | moderate | 8.05854E−05 |
| Event 8 | 5 | 0.00 | 0.00 | 5 | 6.40 | 3.71 | Very weak | 0.018265991 |
| Event 9 | 5 | 2.60 | 2.41 | 5 | 36.60 | 21.03 | weak | 0.022931034 |
| Event 10 | 5 | 1.80 | 3.49 | 5 | 230.80 | 63.93 | strong | 0.001325094 |

*t-Test: Two-Sample Assuming Unequal Variances

ORF256 protein is quantified on Western blot using polyclonal antibodies raised against synthetic ORF256 protein. The knock-out of the Rf1-PPR-09 gene leads to increased accumulation of the ORF256 protein. In the second assay pollen accumulation and pollen viability is quantified using the AmphaZ30 device. The knock-out of the Rf1-PPR-09 gene leads to lower numbers of viable pollen. In the third assay the integrity of anther tissues is inspected microscopically. The knock-out of the Rf1-PPR-09 gene leads to early deterioration of the tapetum layer. In the fourth assay seed set per ear from self-pollination is quantified. The knock-out of the Rf1-PPR-09 gene leads to reduced number of grains per ear. In all tests the F1 progeny from crosses of non-edited Rf plants to the same spring wheat line serve as a control.

Alternatively, guide RNAs for CRISPR-mediated gene editing targeting the promoter region comprised within the nucleotide sequence of SEQ ID NO: 1 from nucleotide position 1 to 3000 are designed and tested in wheat protoplasts of a wheat line of interest in the manner described above. The one or two most efficient guide RNAs are used for stable gene editing in same wheat line as described above, but additionally repair DNA comprising the substation, insertion or deletion of interest (one or more nucleotides) between flanking sequences homologous to the target DNA are also introduced. Plants comprising the edited upstream region are identified by PCR amplification and sequencing and tested for the level of male fertility as described above.

BACKGROUND REFERENCES

Binder, S., Stoll, K., and Stoll, B. (2013). P-class pentatricopeptide repeat proteins are required for efficient 5' end formation of plant mitochondrial transcripts. RNA Biol. 10, 1511-1519.

Chen, J., Zheng, Y., Qin, L., Wang, Y., Chen, L., He, Y., Fei, Z., and Lu, G. (2016). Identification of miRNAs and their targets through high-throughput sequencing and degradome analysis in male and female *Asparagus officinalis*. BMC Plant Biol. 16, 80.

Ding, J., Lu, Q., Ouyang, Y., Mao, H., Zhang, P., Yao, J., Xu, C., Li, X., Xiao, J., and Zhang, Q. (2012). A long noncoding RNA regulates photoperiod-sensitive male sterility, an essential component of hybrid rice. Proc. Natl. Acad. Sci. 109, 2654-2659.

Fang, Y.-N., Zheng, B.-B., Wang, L., Yang, W., Wu, X.-M., Xu, Q., and Guo, W.-W. (2016). High-throughput sequencing and degradome analysis reveal altered expression of miRNAs and their targets in a male-sterile cybrid pummelo (*Citrus grandis*). BMC Genomics 17, 591.

Schmitzlinneweber, C., and Small, I. (2008). Pentatricopeptide repeat proteins: a socket set for organelle gene expression. Trends Plant Sci. 13, 663-670.

Wei, M., Wei, H., Wu, M., Song, M., Zhang, J., Yu, J., Fan, S., and Yu, S. (2013). Comparative expression profiling of miRNA during anther development in genetic male sterile and wild type cotton. BMC Plant Biol. 13, 66.

Wei, X., Zhang, X., Yao, Q., Yuan, Y., Li, X., Wei, F., Zhao, Y., Zhang, Q., Wang, Z., Jiang, W., et al. (2015). The miRNAs and their regulatory networks responsible for pollen abortion in Ogura-CMS Chinese cabbage revealed by high-throughput sequencing of miRNAs, degradomes, and transcriptomes. Front. Plant Sci. 6.

Xia, R., Meyers, B. C., Liu, Z., Beers, E. P., Ye, S., and Liu, Z. (2013). MicroRNA Superfamilies Descended from miR390 and Their Roles in Secondary Small Interfering RNA Biogenesis in Eudicots. Plant Cell Online 25, 1555-1572.

The invention claimed is:

1. A nucleic acid molecule comprising a functional restorer gene allele for wheat G-type cytoplasmic male sterility, wherein said functional restorer gene allele comprises a coding sequence operably-linked to a plant-expressible promoter and to a transcription termination and polyadenylation region,
wherein said coding sequence encodes a polypeptide comprising an amino acid sequence having at least 95% sequence identity to SEQ ID NO: 5, said sequence identity being determined by aligning two sequences over the entire length according to the Needleman and Wunsch global alignment algorithm using default settings,
wherein at least one of said operably linked elements is heterologous with respect to at least one other element, or wherein at least one of said operably linked elements comprises a nucleic acid that has been modified by inserting, deleting or substituting one or more nucleotides in the native nucleic acid, and
wherein:
a) said plant-expressible promoter comprises the sequence of SEQ ID NO: 1 from the nucleotide at position 1 to the nucleotide at position 1000, or
b) said transcription termination and polyadenylation region comprises the sequence of SEQ ID NO: 4 from the nucleotide at position 2434 to the nucleotide at position 3827.

2. The nucleic acid molecule of claim 1, wherein said plant-expressible promoter comprises the sequence of SEQ ID NO: 1 from the nucleotide at position 1 to the nucleotide at position 1000.

3. The nucleic acid molecule of claim 1, wherein said transcription termination and polyadenylation region comprises the sequence of SEQ ID NO: 4 from the nucleotide at position 2434 to the nucleotide at position 3827.

4. The nucleic acid molecule of claim 1, wherein said functional restorer gene allele encodes the polypeptide of SEQ ID NO: 5, or a polypeptide having at least 99% sequence identity to the amino acid sequence of SEQ ID NO: 5, said sequence identity being determined by aligning two sequences over the entire length according to the Needleman and Wunsch global alignment algorithm using default settings.

5. The nucleic acid molecule of claim 1, wherein said modified nucleic acid molecule was modified by genome editing, EMS mutagenesis or radiation induced mutagenesis.

6. The nucleic acid of claim 1,
wherein said plant-expressible promoter is capable of directing expression of the operably linked nucleic acid at least during early pollen development and meiosis, in anther, tapetum, or developing microspores.

7. A wheat plant cell or plant or seed thereof, comprising the nucleic acid molecule of claim 1.

8. A method for producing a wheat plant cell or plant or seed thereof, comprising a functional restorer gene for wheat G-type cytoplasmic male sterility, or for increasing restoration capacity for wheat G-type cytoplasmic male sterility in a wheat plant, comprising the step of providing said plant cell or plant with the nucleic acid molecule of claim 1, wherein said step of providing comprises providing by transformation, crossing, backcrossing, genome editing or mutagenesis.

9. A method for selecting a wheat plant comprising a functional restorer gene allele for wheat G-type cytoplasmic male sterility or for producing a wheat plant comprising a functional restorer gene allele for wheat G-type cytoplasmic male sterility, comprising the steps of:
a. identifying the presence, or expression, or transcription, of a nucleic acid molecule of claim 1 through measuring the level of RNA transcribed or through DNA detection methods; and
b. selecting the plant comprising and expressing said at least one marker allele, wherein said plant comprises said functional restorer gene for wheat G-type cytoplasmic male sterility located on chromosome 1A.

10. A method for identifying and/or selecting wheat plant comprising a functional restorer gene allele for wheat G-type cytoplasmic male sterility comprising the steps of
a. identifying or detecting in said plant the presence, the expression or the transcription of a nucleic acid of claim 1;
b. and optionally selecting said plant comprising or expressing or transcribing said nucleic acid.

11. A method for producing hybrid seed, comprising the steps of:
a. providing a male wheat parent plant according to claim 7, said plant comprising or expressing said functional restorer gene allele for wheat G-type cytoplasmic male sterility, wherein said functional restorer gene allele is preferably present in homozygous form;
b. providing a female wheat parent plant that is a G-type cytoplasmic male sterile wheat plant;
c. crossing said female wheat parent plant with a said male wheat parent plant; and
d. harvesting seeds.

12. The nucleic acid molecule of claim 1, wherein heterologous refers to said operably-linked elements being from different sources, or refers to modifying a native promoter to include regulatory elements that increase transcription, or modifying a native promoter by inactivating or removing certain negative regulatory elements, and wherein:
a) said plant-expressible promoter comprises the sequence of SEQ ID NO: 1 from the nucleotide at position 1 to the nucleotide at position 1000, or
b) said transcription termination and polyadenylation region comprises the sequence of SEQ ID NO: 4 from the nucleotide at position 2434 to the nucleotide at position 3827.

13. The nucleic acid molecule of claim 1, wherein at least one of said operably linked elements is heterologous with respect to at least one other element, and wherein:
a) said plant-expressible promoter comprises the sequence of SEQ ID NO: 1 from the nucleotide at position 1 to the nucleotide at position 1000, or
b) said transcription termination and polyadenylation region comprises the sequence of SEQ ID NO: 4 from the nucleotide at position 2434 to the nucleotide at position 3827.

14. The nucleic acid molecule of claim 1, wherein at least one of said operably linked elements comprises a nucleic acid that has been modified by inserting, deleting or substituting one or more nucleotides in the native nucleic acid, and wherein:
a) said plant-expressible promoter comprises the sequence of SEQ ID NO: 1 from the nucleotide at position 1 to the nucleotide at position 1000, or
b) said transcription termination and polyadenylation region comprises the sequence of SEQ ID NO: 4 from the nucleotide at position 2434 to the nucleotide at position 3827.

15. A method for converting a non-restoring wheat plant into a restoring plant for wheat G-type cytoplasmic male sterility, comprising the step of modifying the genome of said plant to comprise and/or express the nucleic acid molecule of claim 1, wherein said step of modifying comprises modifying by transformation, crossing, backcrossing, genome editing or mutagenesis.

16. A method for restoring fertility in progeny of a G-type cytoplasmic male sterile wheat plant or for producing a fertile progeny plant from a G-type cytoplasmic male sterile wheat parent plant, comprising the steps of:
 a. providing a population of progeny plants obtained from crossing a female wheat parent plant with a male wheat parent plant, wherein the female parent plant is a G-type cytoplasmic male sterile wheat plant, and wherein the male parent plant comprises and/or expresses the nucleic acid of claim 1;
 b. identifying in said population a fertile progeny plant comprising and/or expressing the nucleic acid of claim 1; and
 c. selecting said fertile progeny plant; and optionally propagating the fertile progeny plant.

17. The plant of claim 7, wherein said plant comprises a further functional restorer gene for wheat G-type cytoplasmic male sterility, wherein said further functional restorer gene is Rf2, Rf3, Rf4, Rf5, Rf6, Rf7, or Rf8.

18. A method for producing a wheat plant, comprising a functional restorer gene allele for wheat G-type cytoplasmic male sterility, comprising the steps of:
 a. crossing a first wheat with a second wheat plant, wherein said first wheat plant is the plant of claim 7; and
 b. identifying and selecting a progeny plant comprising the nucleic acid of claim 1.

19. The method of claim 10, wherein said nucleic acid is expressed at least during early pollen development and meiosis, in anther, tapetum, or developing microspores.

20. A wheat plant cell or plant or seed thereof, comprising the nucleic acid molecule of claim 12, or expressing the polypeptide encoded by said nucleic acid molecule, wherein said polypeptide has increased expression in said plant, plant cell or seed, or said polypeptide is heterologous with respect to said plant cell or plant or seed.

21. A method for producing a wheat plant cell or plant or seed thereof, comprising a functional restorer gene for wheat G-type cytoplasmic male sterility, or for increasing restoration capacity for wheat G-type cytoplasmic male sterility in a wheat plant, comprising the step of providing said plant cell or plant with the nucleic acid molecule of claim 12, wherein said step of providing comprises providing by transformation, crossing, backcrossing, genome editing or mutagenesis.

22. A wheat plant cell or plant or seed thereof, comprising and/or expressing the nucleic acid molecule of claim 1 and the polypeptide encoded by said nucleic acid molecule, wherein said polypeptide has increased expression in said plant, plant cell or seed, or said polypeptide is heterologous with respect to said plant cell or plant or seed.

23. A wheat plant cell or plant or seed thereof comprising and/or expressing the nucleic acid molecule of claim 12 and the polypeptide encoded by said nucleic acid molecule, wherein said polypeptide has increased expression in said plant, plant cell or seed, or said polypeptide is heterologous with respect to said plant cell or plant or seed.

24. The plant cell, plant or seed of claim 22, wherein the polypeptide is expressed at least during early pollen development and meiosis.

25. The plant cell, plant or seed of claim 24, which is a hybrid plant cell, plant or seed.

26. The plant cell, plant or seed of claim 23, wherein the polypeptide is expressed at least during early pollen development and meiosis.

27. The plant cell, plant or seed of claim 26, which is a hybrid plant cell, plant or seed.

* * * * *